United States Patent
Zheng et al.

(10) Patent No.: US 10,300,151 B2
(45) Date of Patent: May 28, 2019

(54) METHODS AND SYSTEMS FOR NONINVASIVE FLUORESCENCE-BASED FUNCTIONAL IMAGING OF KIDNEYS

(71) Applicant: Board of Regents, The University of Texas System, Austin, TX (US)

(72) Inventors: Jie Zheng, Allen, TX (US); Mengxiao Yu, Plano, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 269 days.

(21) Appl. No.: 15/262,307

(22) Filed: Sep. 12, 2016

(65) Prior Publication Data

US 2017/0072073 A1    Mar. 16, 2017

Related U.S. Application Data

(60) Provisional application No. 62/217,435, filed on Sep. 11, 2015.

(51) Int. Cl.
*A61K 49/00* (2006.01)
*A61B 5/00* (2006.01)

(52) U.S. Cl.
CPC ........ *A61K 49/0065* (2013.01); *A61B 5/0071* (2013.01); *A61B 5/4222* (2013.01); *A61B 5/7275* (2013.01); *A61K 49/0004* (2013.01); *A61K 49/0056* (2013.01); *A61B 2503/40* (2013.01); *A61B 2503/42* (2013.01)

(58) Field of Classification Search
None
See application file for complete search history.

(56) References Cited

U.S. PATENT DOCUMENTS

| | | | | |
|---|---|---|---|---|
| 5,928,625 A | * | 7/1999 | Dorshow | A61K 49/0034 424/1.11 |
| 8,409,863 B2 | * | 4/2013 | Natan | G01N 21/658 436/171 |
| 9,398,876 B2 | * | 7/2016 | Wang | A61B 5/0071 |
| 2014/0099256 A1 | * | 4/2014 | Zheng | A61K 49/0002 424/1.29 |
| 2014/0193837 A1 | | 7/2014 | Zheng | |

OTHER PUBLICATIONS

Paul Alivisatos, Semiconductor clusters, nanocrystals, and quantum dots, Science 271, 933-937 (1996), Berkeley CA.

(Continued)

*Primary Examiner* — Brian T Gedeon
(74) *Attorney, Agent, or Firm* — Parker Highlander PLLC

(57) ABSTRACT

Methods and systems for evaluating renal function of a live subject. The method includes intravenously administering nanoparticles of a noble metal to the kidney of the live subject, followed by illuminating the kidney with a near infrared excitation wavelength such that the nanoparticles in the kidney fluoresce, and finally detecting presence or absence of nanoparticle fluorescence in the kidney. Detecting presence or absence of nanoparticle fluorescence includes obtaining at least one image of the kidney through the subject's skin.

20 Claims, 32 Drawing Sheets
(31 of 32 Drawing Sheet(s) Filed in Color)

(56) References Cited

OTHER PUBLICATIONS

Hak Soo Choi, Summer L. Gibbs, Jeong Heon Lee, Soon Hee Kim, Yoshitomo Ashitate, Fangbing Liu, Hoon Hyun, Gwangli Park, Yang Xie, Soochan Bae, Maged Henary, John V. Frangioni. Targeted zwitterionic near-infrared fluorophores for improved optical imaging, Nature Biotechnology 31, 148-153 (2013), Boston, MA.
Hak Soo Choi, Wenhao Liu, Preeti Misra, Eiichi Tanaka, John P Zimmer, Binil Itty Ipe, Moungi G Bawendi, John V Frangioni, Renal clearance of quantum dots, Nature Biotechnology 25, 1165-1170 (2007), Boston, MA.
Leo Y. T. Chou, Kyryl Zagorovsky, Warren C. W. Chan, DNA assembly of nanoparticle superstructures for controlled biological delivery and elimination, Nature Nanotechnology 9, 148-155 (2014), Ontario, Canada.
Sungjin Chung, Hye Eun Yoon, Soo Jeong Kim, Sung Jun Kim, Eun Sil Koh, Yu Ah Hong, Cheol Whee Park, Yoon Sik Chang, Seok Joon Shin, Oleanolic acid attenuates renal fibrosis in mice with unilateral ureteral obstruction via facilitating nuclear translocation of Nrf2, Nutrition & Metabolism 11, 2 (2014).
J. Conway, Max Maizels, The Well Tempered Diuretic Renogram—A Standard Method to Examine the Asymptomatic Symptomatic Neonate with Hydronephrosis or Hydroureteronephrosis. J. Nucl. Med. 33, 2047-2051 (1992).
Yong Du, Shion An, Li Liu, Li Li, Xin J. Zhou, Ralph P. Mason, Chandra Mohan, Serial Non-Invasive Monitoring of Renal Disease Following Immune-Mediated Injury Using Near-Infrared Optical Imaging, Plos One 7, e43941 (2012), Dallas, Texas.
John V Frangioni, In vivo near-infrared fluorescence imaging, Current Opinion in Chemical Biology 7, 626-634 (2003).
Xiaohu Gao, Yuanyuan Cui, Richard M Levenson, Leland W K Chung, Shuming Nie, In vivo cancer targeting and imaging with semiconductor quantum dots. Nature Biotechnology 22, 969-976 (2004), United States.
Chen Zhou, Michael Long, Yanping Qin, Xiankai Sun, Jie Zheng, Luminescent Gold Nanoparticles with Efficient Renal Clearance. Angewandte Chemie—International Edition 50, 3168-3172 (2011).
Guiyang Hao, Yong Du, Xin J. Zhou, Jianfei Guo, Xiankai Sun, Chandra Mohan, Orhan K. Öz, Serial Non-Invasive Assessment of Antibody Induced Nephritis in Mice Using Positron Emission Tomography. Plos One 8 (2013).
Scott Hilderbrand, Ralph Weissleder, Near-infrared fluorescence: application to in vivo molecular imaging. Current Opinion in Chemical Biology 14, 71-79 (2010).
Guosong Hong, Shuo Diao, Junlei Chang, Alexander L. Antaris, Changxin Chen, Bo Zhang, Su Zhao, Dmitriy N. Atochin, Paul L. Huang, Katrin I. Andreasson, Calvin J. Kuo, Hongjie Dai, Through-skull fluorescence imaging of the brain in a new near-infrared window. Nature Photonics 8, 723-730 (2014).
Matthew T James, Brenda R Hemmelgarn, Marcello Tonelli, Renal Medicine 2 Early recognition and prevention of chronic kidney disease. Lancet 375, 1296-1309 (2010).
F. Khan, K. Ahmed, N. Lee, B. Challacombe, M.S. Khan, P. Dasgupta, Management of ureteropelvic junction obstruction in adults. Nat Rev Urol 11, 629-638 (2014).
Kazuki Kiyose, Kenjiro Hanaoka, Daihi Oushiki, Tomomi Nakamura, Mayumi Kajimura, Makoto Suematsu, Hiroaki Nishimats, Takehiro Yamane, Takuya Terai, Yasunobu Hirata, Tetsuo Nagano, Hypoxia-Sensitive Fluorescent Probes for in Vivo Real-Time Fluorescence Imaging of Acute Ischemia. Journal of the American Chemical Society 132, 15846-15848 (2010).
Demin Liu, Christopher Poon, Kuangda Lu, Chunbai He, Wenbin Lin, Self-assembled nanoscale coordination polymers with trigger release properties for effective anticancer therapy. Nature Communications 5 (2014).
Jinbin Liu, Mengxiao Yu, Chen Zhou, Shengyang Yang, Xuhui Ning, Jie Zheng, Passive Tumor Targeting of Renal-Clearable Luminescent Gold Nanoparticles: Long Tumor Retention and Fast Normal Tissue Clearance. Journal of the American Chemical Society 135, 4978-81 (2013), Richardson, Texas.
Jonathan F. Lovell, Cheng S. Jin, Elizabeth Huynh, Honglin Jin, Chulhong Kim, John L. Rubinstein, Warren C. W. Chan, Weiguo Cao, Lihong V. Wang, Gang Zheng, Porphysome nanovesicles generated by porphyrin bilayers for use as multimodal biophotonic contrast agents. Nature Materials 10, 324-332 (2011). Nakamura, K. & Tabata, Y. A new fluorescent imaging of renal inflammation with RCP. Journal of Controlled Release 148, 351-358 (2010).
X.-H. Ning, X.-F. Ge, Y. Cui, H.-x. An, Ulinastatin inhibits unilateral ureteral obstruction-induced renal interstitial fibrosis in rats via transforming growth factor β(TGF-β)/Smad signalling pathways. International Immunopharmacology 15, 406-413 (2013).
J.H. Park, Gu, L., von Maltzahn, G., Ruoslahti, E., Bhatia, S.N. & Sailor, M.J. Biodegradable luminescent porous silicon nanoparticles for in vivo applications. Nature Materials 8, 331-336 (2009).
F.J. Penna, J.S. Chow, B.J. Minnillo, C.C. Passerotti, C.E. Barnewolt, S.T. Treves, F.H. Fahey, P.S. Dunning, D.A. Freilich, A.B. Retik, H.T. Nguygen, Identifying Ureteropelvic Junction Obstruction by Fluorescence Imaging: A Comparative Study of Imaging Modalities to Assess Renal Function and Degree of Obstruction in a Mouse Model. Journal of Urology 185, 2405-2413 (2011).
Zchen Zhou, Ce Sun, Mengxiao Yu, Yanping Qin, Jinguo Wang, Moon Kim, Jie Zheng, Luminescent Gold Nanoparticles with Mixed Valence States Generated from Dissociation of Polymeric Au(I) Thiolates. The Journal of Physical Chemistry C 114, 7727-7732 (2010), Richardson, TX.
John Roberts, Bo Chen, Lisa M. Curtis, Anupam Agarwal, Paul W. Sanders, Kurt R. Zinn, Detection of early changes in renal function using (99m)Tc-MAG3 imaging in a murine model of ischemia-reperfusion injury. American Journal of Physiology—Renal Physiology 293, F1408-F1412 (2007).
Courtney K. Rowe, Felipe B. Franco, Joao A. B. A. Barbosa, Brian J. Minnillo, Jeanne S. Chow, Ted Treves, Alan B. Retik, Hiep T. Nguyen, A Novel Method of Evaluating Ureteropelvic Junction Obstruction: Dynamic Near Infrared Fluorescence Imaging Compared to Standard Modalities to Assess Urinary Obstruction in a Swine Model. Journal of Urology 188, 1978-1985 (2012).
Sya-Ping Sun, Bing Zhou, Yi Lin, Wei Wang, K. A. Shiral Fernando, Pankaj Pathak, Mohammed Jaouad Meziani, Barbara A. Harruff, Xin Wang, Haifang Wang, Pengju G. Luo, Hua Yang, Muhammet Erkan Kose, Bailin Chen, L. Monica Veca, Su-Yuan Xie. Quantum-sized carbon dots for bright and colorful photoluminescence. Journal of the American Chemical Society 128, 7756-7757 (2006).
Z. Szabo, N. Alachkar, J.S. Xia, W.B. Mathews, H. Rabb, Molecular Imaging of the Kidneys. Seminars in Nuclear Medicine 41, 20-28 (2011).
Mohammed N Tantawy, Rosie Jiang, Feng Wang, Keiko Takahashi, Todd E Peterson, Dana Zemel, Chuan-Ming Hao, Hiroki Fujita, Raymond C Harris, Christopher C Quarles, Takamune Takahashi, Assessment of renal function in mice with unilateral ureteral obstruction using Tc-99m-MAG3 dynamic scintigraphy. Bmc Nephrology 13 (2012).
TK.J. Tobis, CR Silvers, J Marshall, A Cardin, RW Wood, JE Reeder, E Erturk, R Madeb, J Yao, EA Singer, H Rashid, G Wu, E Messing, D Golijanin, Near infrared fluorescence imaging after intravenous indocyanine green: initial clinical experience with open partial nephrectomy for renal cortical tumors. Urology 79, 7 (2012).
Igor I. Vlasov, Andrey A. Shiryaev, Torsten Rendler, Steffen Steinert, Sang-Yun Lee, Denis Antonov, Márton Vörös, Fedor Jelezko, Anatolii V. Fisenko, Lubov F. Semjonova, Johannes Biskupek, Ute Kaiser, Oleg I. Lebedev, Ilmo Sildos, Philip. R. Hemmer, Vitaly I. Konov, Adam Gali, Jörg Wrachtru, Molecular-sized fluorescent nanodiamonds. Nature Nanotechnology 9, 54-58 (2014).
Ralph Weissleder, Mikael J. Pittet, Imaging in the era of molecular oncology. Nature 452, 580-589 (2008).
William L. Wilson, P. F. Szajowski, L. E. Brus, Quantum Confinement in Size-Selected, Surface-Oxidized Silicon Nanocrystals. Science 262, 1242-1244 (1993).
Mengxiao Yu, Chen Zhou, Jinbin Liu, Julia D. Hankins, Jie Zheng, Luminescent Gold Nanoparticles with pH-Dependent Membrane Adsorption. Journal of the American Chemical Society 133, 11014-11017 (2011), Richardson, Texas.

(56) References Cited

OTHER PUBLICATIONS

Zjie Zheng, Philip R. Nicovich, Robert M. Dickson, Highly fluorescent noble-metal quantum dots. Annual Review of Physical Chemistry 58, 409-431 (2007).

Jie Zheng, Chen Zhou, Mengxiao Yu, Jinbin Liu, Different sized luminescent gold nanoparticles. Nanoscale 4, 4073-4083 (2012).

Chen Zhou, Guiyang Hao, Patrick Thomas, Jinbin Liu, Mengxiao Yu, Shasha Sun, Orhan K. Öz, Xiankai Sun, Jie Zheng, Near-Infrared Emitting Radioactive Gold Nanoparticles with Molecular Pharmacokinetics. Angewandte Chemie—International Edition 51, 10118-10122 (2012).

* cited by examiner

IRDye® 800CW
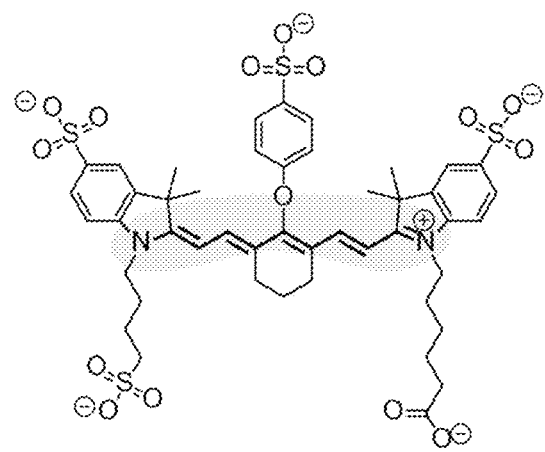
GS-AuNP
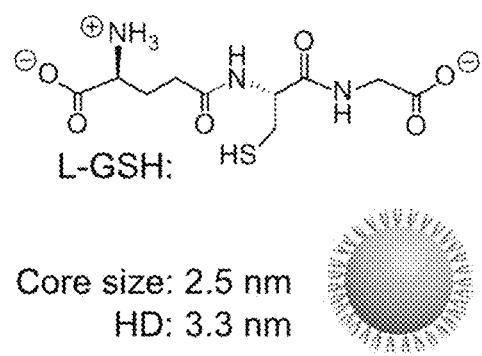
L-GSH:
Core size: 2.5 nm
HD: 3.3 nm
Fig. 15

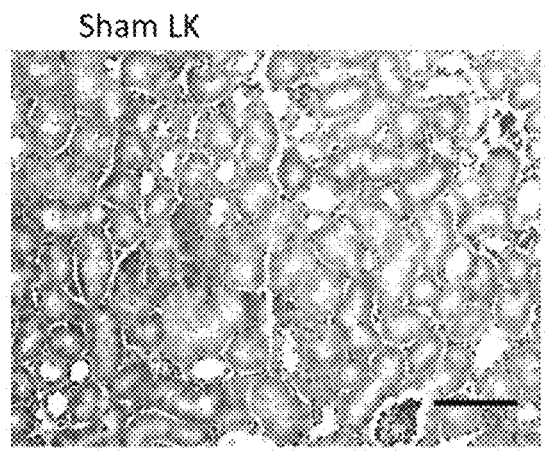
Fig. 47 — Sham LK
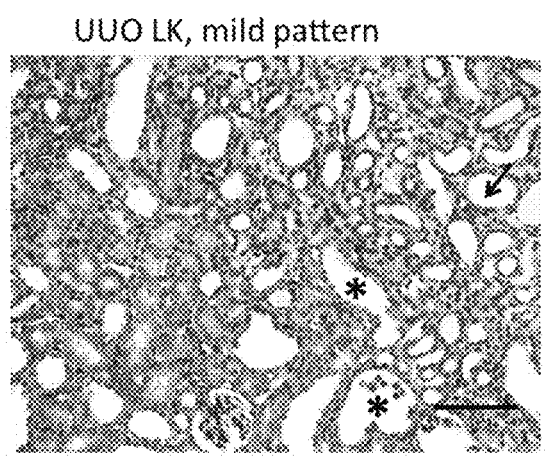
Fig. 48 — UUO LK, mild pattern
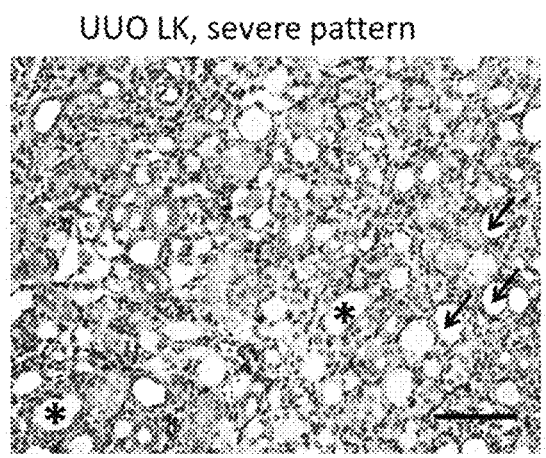
Fig. 49 — UUO LK, severe pattern

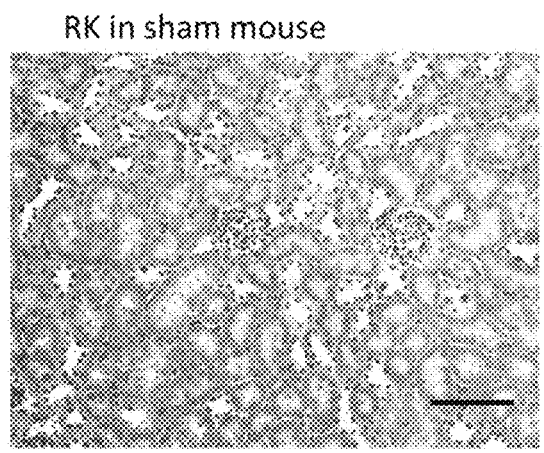
Fig. 51 RK in sham mouse
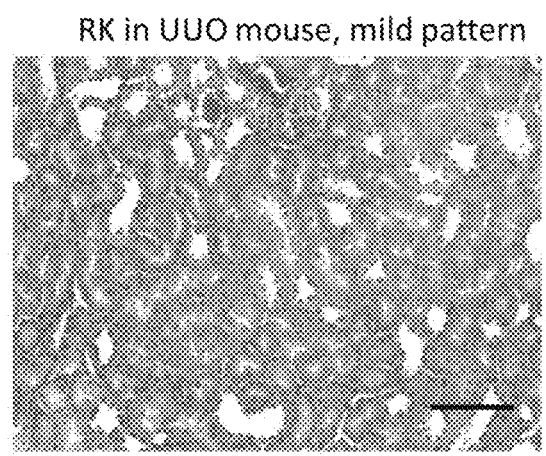
Fig. 52 RK in UUO mouse, mild pattern
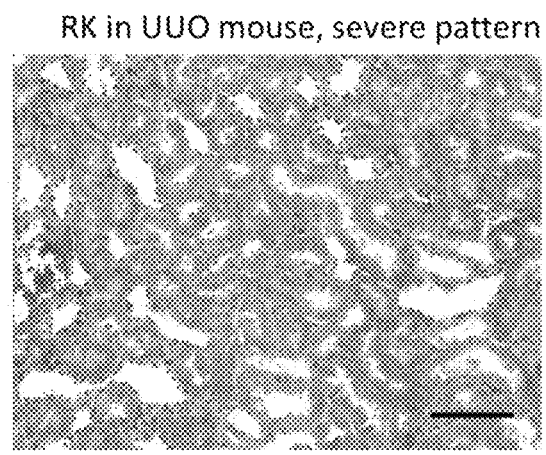
Fig. 53 RK in UUO mouse, severe pattern

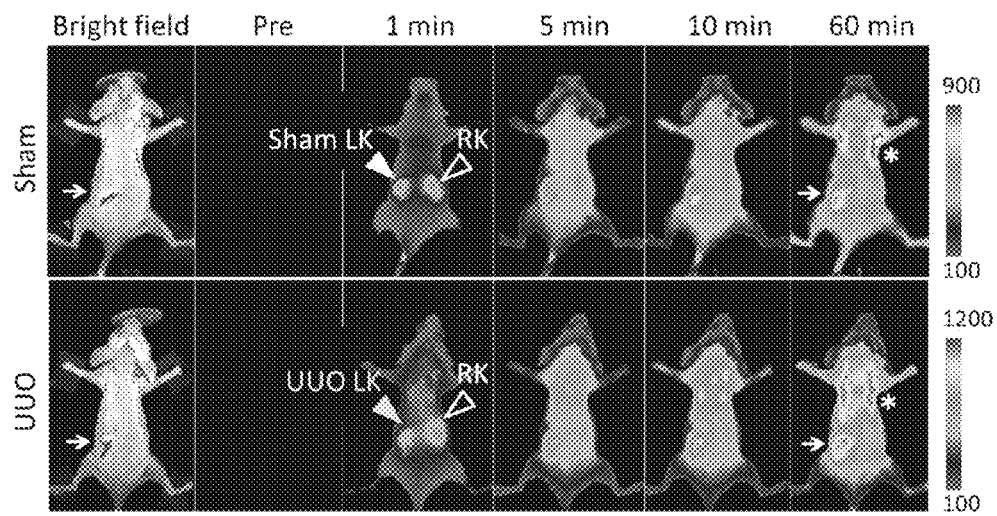
Fig. 55
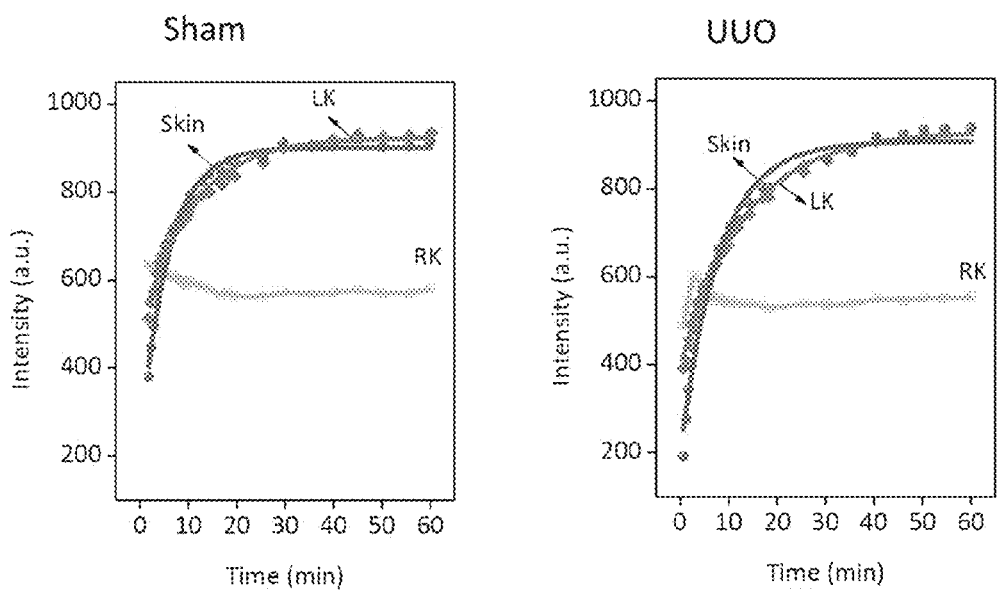
Fig. 56                    Fig. 57

METHODS AND SYSTEMS FOR NONINVASIVE FLUORESCENCE-BASED FUNCTIONAL IMAGING OF KIDNEYS

CROSS-REFERENCE TO RELATED APPLICATION

The present application claims benefit of and priority to U.S. Provisional Patent Application Ser. No. 62/217,435 filed on Sep. 11, 2015 entitled "Methods and Systems for Noninvasive Fluorescence-based Functional Imaging of Kidneys," the entire contents of which are hereby incorporated by reference herein.

STATEMENT REGARDING FEDERALLY-SPONSORED RESEARCH OR DEVELOPMENT

This invention was made with government support under Grant Nos. R21EB011762, R21EB009853, and 1R01DK103363 awarded by the National Institutes of Health and Grant No. RP120588 awarded by Cancer Prevention and Research Institute of Texas. The government has certain rights in the invention.

BACKGROUND

Kidney diseases affect >10% of adults worldwide but fundamental understanding of kidney pathogenesis relies on high-cost and less-accessible radiological imaging techniques. A possible alternative, in vivo noninvasive fluorescence imaging, falls short as a low-cost, high-sensitivity tool for longitudinal evaluation of kidney function of small animals. Noninvasive fluorescence kidney functional imaging is deficient, not due to the limited penetration depth of the light, but rather the undesired rapid accumulation of conventional organic fluorophores in background tissues.

Development of low-cost imaging techniques for noninvasive longitudinal assessment of individual kidney function is indispensable to understand the pathogenesis of kidney disease and accelerate drug discovery. In both clinical practice and preclinical research, measuring blood urea nitrogen (BUN) and serum creatinine (Scr) concentrations is the most common and low-cost method for evaluation of kidney function. However, blood tests often fail to identify the kidney function changes at an early asymptomatic stage, particularly in unilateral renal disease where a contralateral kidney functions well. To address this challenge, renography, a noninvasive kidney functional imaging technique, has been widely used in longitudinal monitoring of disease progresses of individual kidneys at high spatial and temporal resolution,[4] which generally includes the following steps: 1) continuous imaging of kidneys for ~60 min right after intravenous (i.v.) injection of a renal clearable probe; 2) conversion of the obtained images to time-intensity curves of each kidney (renograms); 3) derivation of accumulation and clearance kinetics of the injected probe from renograms. Since accuracy of kidney functional evaluation requires imaging of accumulation and clearance of renal clearable probes in the kidneys at high contrast and high temporal resolution, very few probes except radiotracers can meet this requirement even in the preclinical research. However, high cost and potential radiation exposure make radiological imaging techniques less accessible for most researchers and severely limit fundamental understanding of kidney diseases.

In vivo NIR fluorescence imaging allows visualization of biological processes in intact living animals at high spatial and temporal resolution. This technique has been widely used in preclinical disease studies due to its low cost, high sensitivity and the absence of radiation. However, translation of fluorescence techniques into noninvasive kidney functional imaging remains highly challenging. Due to extremely low contrast in noninvasive images of the kidney, kidney fluorescence imaging studies which utilize renal clearable organic fluorophores as contrast agents suffer one of two possible restrictions: (1) the studies must be conducted invasively (the kidneys are surgically exposed); or (2) the fluorophores must be conjugated with ligands which target specific receptors in the kidneys.

BRIEF SUMMARY OF THE INVENTION

One example of the current invention is a method for evaluating renal function of a live subject. The method includes intravenously administering nanoparticles of a noble metal to the kidney of the live subject, followed by illuminating the kidney with a near infrared excitation wavelength such that the nanoparticles in the kidney fluoresce, and finally detecting presence or absence of nanoparticle fluorescence in the kidney. Detecting presence or absence of nanoparticle fluorescence includes obtaining at least one image of the kidney through the subject's skin.

Another example of the current invention is a system for evaluating renal function of a live subject comprising intravenous administration of nanoparticles of a noble metal to the kidney of the subject, illumination of the kidney with a near infrared excitation wavelength such that the nanoparticles in the kidney fluoresce, and detection of presence or absence of nanoparticle fluorescence in the kidney of the live subject, wherein detection includes obtaining at least one image of the kidney through the subject's skin.

Another embodiment of the current invention is a kit comprising: an amount of nanoparticles of a noble metal in a sealed container, wherein the amount of the nanoparticles is suitable for imaging a kidney of a live subject and wherein the noble metal is selected from a group consisting of gold, silver, copper, or combinations thereof, and instructions for the nanoparticles for imaging of the kidney. The instructions include the following steps:

a) administering the nanoparticles to the kidney of the live subject;

b) illuminating the kidney with a near infrared excitation wavelength such that the nanoparticles in the kidney fluoresce; and c) detecting presence or absence of nanoparticle fluorescence in the kidney of the live subject.

Detecting presence or absence of nanoparticle fluorescence would include obtaining at least one image of the kidney through the subject's skin. Furthermore taking at least one image of the kidney includes taking sequential images within an evaluation time window.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 13 was generated from the same data set as FIGS. 6-7.

FIG. 14 was generated from the same data set as FIGS. 8-9.

FIG. 15 shows the chemical structure of IRDye 800CW carboxylate (also referred herein as IRDye 800CW) and a schematic representation of NIR-emitting gold nanoparticles with glutathione (GSH)-coated surfaces (GS-AuNP).

FIGS. 27 and 28 also show deconvolution of the curves into two peaks. The first (sharp) peak and second peak correspond with the vascular phase and tubular phase of GS-AuNP clearance through the kidney, respectively.

FIG. 29 shows a statistical comparison of vascular phase peak values extracted from noninvasive and invasive kidney time-fluorescence intensity curves (FIGS. 27 and 28). "*" indicates P<0.05.

FIG. 30 shows a statistical comparison of tubular phase peak values extracted from noninvasive and invasive kidney time-fluorescence intensity curves (FIGS. 27 and 28). "*" indicates P<0.05.

FIG. 31 shows a statistical comparison of the decay half-life values for the tubular phase extracted from noninvasive and invasive kidney time-fluorescence intensity curves (FIGS. 27 and 28). "*" indicates P<0.05.

FIG. 32 shows the percentage of relative renal function (% RRF) in the vascular phase, as obtained from noninvasive and invasive kidney time-fluorescence intensity curves (FIGS. 27 and 28). % RRF=[peak value of LK or RK/(peak value of LK+peak value of RK)]×100%. "NS" indicates that there is no significant difference between the values obtained from invasive and non-invasive imaging techniques.

FIG. 33 shows the percentage of relative renal function (% RRF) in the tubular phase, as obtained from noninvasive and invasive kidney time-fluorescence intensity curves (FIGS. 27 and 28). "NS" indicates that there is no significant difference between the values obtained from invasive and non-invasive imaging techniques.

FIG. 34 shows the peak times in the vascular phase, as obtained from noninvasive and invasive kidney time-fluorescence intensity curves (FIGS. 27 and 28). "NS" indicates that there is no significant difference between the values obtained from invasive and non-invasive imaging techniques.

FIG. 35 shows the peak times in the tubular phase, as obtained from noninvasive and invasive kidney time-fluorescence intensity curves (FIGS. 27 and 28). "NS" indicates that there is no significant difference between the values obtained from invasive and non-invasive imaging techniques.

FIG. 36 shows noninvasive fluorescence imaging of a unilateral ureter obstruction (UUO) mouse and a sham control mouse after intravenous injection of GS-AuNPs. The leftmost panels show bright field images of the mice prior to intravenous injection. The rest of the panels show noninvasive fluorescence images of the mice before injection with GS-AuNPs (Pre) and at 1 min, 5 min, and 60 min post injection.

FIG. 37 shows time-fluorescence intensity curves (TFICs) of the obstructed left kidney of a UUO mouse (UUO LK), the left kidney of a sham control mouse (Sham LK), and contralateral (unobstructed) right kidneys of the UUO mouse (RK in UUO mouse) and the sham mouse (RK in sham mouse). Noninvasive imaging was performed after intravenous injection of GS-AuNPs.

FIGS. 38-44 show an assessment of the functional change of each kidney of the UUO mouse by statistically comparing parameters extracted from the TFICs/renograms in FIG. 37. In panels c-i, N=6 for UUO mice, N=3 for sham control, mean±s.d., *P<0.05, P<0.01, *P<0.0001; NS, no significant difference.

FIG. 38 shows a statistical comparison of vascular phase peak values of GS-AuNP clearance through the kidney, which were extracted from the TFICs/renograms in FIG. 37.

FIG. 39 shows a statistical comparison of tubular phase peak values of GS-AuNP clearance through the kidneys, which were extracted from the TFICs/renograms in FIG. 37.

FIG. 40 shows a statistical comparison of percentage of relative renal function (% RRF) in the vascular phase of GS-AuNP clearance through the kidneys, extracted from the TFICs/renograms in FIG. 37.

FIG. 41 shows a statistical comparison of percentage of relative renal function (% RRF) in the tubular phase of GS-AuNP clearance through the kidneys, which were extracted from the TFICs/renograms FIG. 37.

FIG. 42 shows a statistical comparison of percentage of peak times in the vascular phase of GS-AuNP clearance through the kidneys, extracted from the TFICs/renograms in FIG. 37.

FIG. 43 shows a statistical comparison of percentage of peak times in the tubular phase of GS-AuNP clearance through the kidneys, which were extracted from the TFICs/renograms in FIG. 37.

FIG. 44 shows decay half-lives corresponding to the tubular phase of GS-AuNP clearance through the kidneys, extracted from the TFICs/renograms in FIG. 37.

FIG. 45 shows ex vivo images of the kidneys characterized in FIGS. 36-44.

FIGS. 47-49 show pathologic analysis of UUO LKs and sham LK (H&E stain, scale bar=100 μm). The analysis revealed no damage to sham LK (FIG. 47), mild to moderate damage to UUO LK (mild pattern) (FIG. 48), and severe damage to UUO LK (severe pattern) (FIG. 49). In FIGS. 47 and 48, the tubular atrophy is depicted by arrows and tubular dilatation by stars.

FIGS. 51-53 show pathologic analysis of sham RK (FIG. 51) and RKs in UUO mice (FIGS. 52-53) (H&E stain, scale bar=100 μm). These RKs and the LKs in FIG. 47-49 originate from the same mice.

FIGS. 55-57 show evaluation of fluorescence imaging of mouse kidneys (in a UUO mouse and in a sham mouse) after IRDye 800CW injection.

FIG. 55 shows brightfield images and fluorescence images of a UUO mouse and a sham control before and after intravenous injection of IRDye 800CW. The brightfield images (Bright field) were collected before GS-AuNPs were injected. These fluorescence images were taken before IRDye 800 CW was injected (Pre) and at 1 min, 5 min, 10 min, and 60 minutes post injection. UUO LK and RK disappeared after 5 min p.i. due to overwhelming fluorescence background from mouse skins skin (star). Dye molecules tended to accumulate in the skin scar area (arrow), where skin became thicker during recovery after surgery.

FIGS. 56-57 shows the time-fluorescence intensity curves of LK, RK and skin of the sham control (FIG. 56) and the UUO mouse (FIG. 57) were very similar in the profile.

DETAILED DESCRIPTION OF THE INVENTION

Figure 1A:
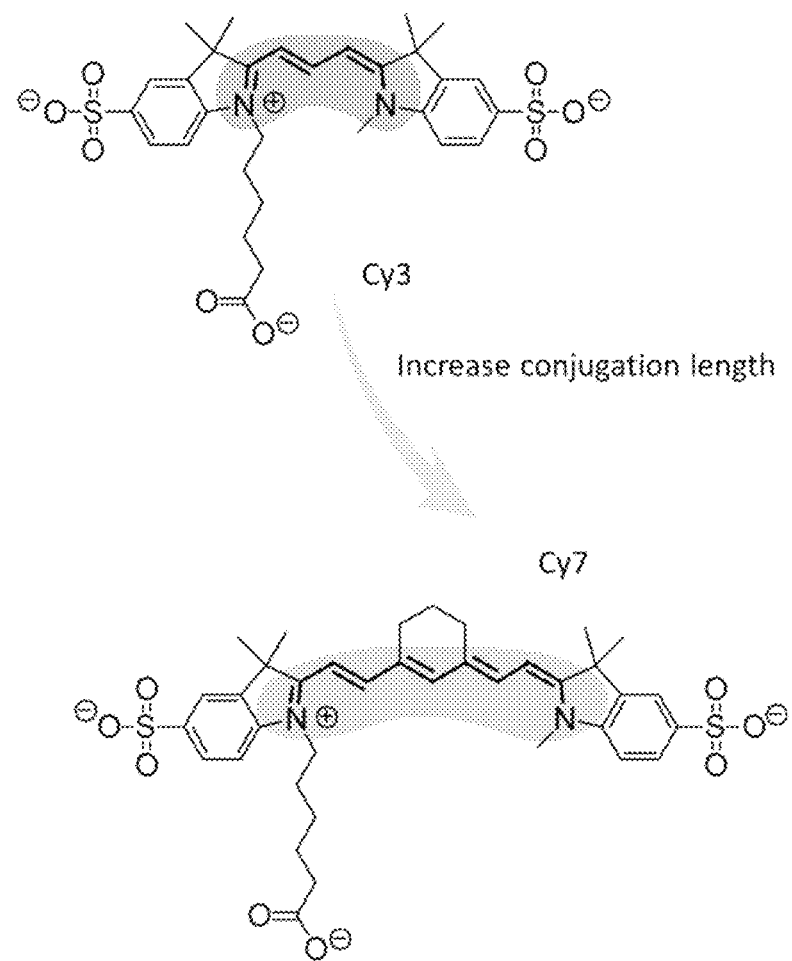
FIG. 1A shows the chemical structures of two commonly-used organic dyes, disulfo-Cy3 carboxylate (Cy3) and disulfo-Cy7 carboxylate (Cy7), highlighting the increase of conjugation length from Cy3 to Cy7.

Accordingly, one example of the current invention is a method for evaluating renal function of a live subject. The method begins by intravenously administering nanoparticles of a noble metal to the kidney of the live subject. According to an embodiment of the invention, the noble metal may be selected from a group consisting of gold, silver, copper, platinum, palladium, or combinations thereof. The nanoparticles may have a hydrodynamic diameter less than 10 nm, possibly between 1 and 6 nm, or between 2 nm and 4 nm.

According to another embodiment of the invention, the live subject may be a non-human mammal, such as a mouse. The nanoparticles may also have a core diameter less than 6 nm, possibly between 1 nm and 4 nm. The nanoparticles may be coated with ligands such as glutathione, thiol-functionalized polyethylene glycol, cysteamine, cysteine, homocysteine, dipeptides containing cysteine (such as cysteine-glycine, cysteine-glutamic acid). The ligands may also be dipeptides (such as homocysteine-glycine and homocysteine-glutamic acid), tripeptides, and combinations of the two or more of the ligands listed herein.

According to another embodiment of the invention, the nanoparticles may be administered intravenously.

After administering the nanoparticles, the method proceeds to illuminating the kidney with a near infrared excitation wavelength such that the nanoparticles in the kidney fluoresces. The nanoparticles may fluoresce in a near infrared emission wavelength.

After illuminating the kidney, the method proceeds to detecting presence or absence of nanoparticle fluorescence in the kidney. Detecting presence or absence of nanoparticle fluorescence includes obtaining at least one image of the kidney through the subject's skin. According to another embodiment of the invention, the image of the kidney may be exhibited on a digital display. Taking at least one image of the kidney may involve taking sequential images within an evaluation time window, which may span 24 or fewer hours after administering the nanoparticles. In exemplary embodiments of the invention, the length of the evaluation time window may be between 1 second and 10 hours, possibly between 0.5 min and 3 hours or between 0.5 min and 60 min.

After detecting the presence or absence of nanoparticle fluorescence in the kidney, the method proceeds to plotting a time-fluorescence intensity curve for the kidney, wherein one axis of the curve is time and the other axis is kidney fluorescence intensity. After deconvolution, the method may proceed to deconvoluting the TFIC into a first component curve and a second component curve. The first component curve may correspond with a vascular phase of nanoparticle clearance from the kidney, and the second component curve may correspond with a tubular phase of nanoparticle clearance from the same kidney.

The method may then proceed to fitting the curve to an exponential decay function. The exponential decay function may either be a single exponential decay function or a double exponential decay function.

After fitting the curve to an exponential decay function, the method proceeds to extracting at least one curve parameter value from exponential decay function. The curve parameter value may be selected from a group consisting of peak value, peak time, decay half-life, and a percentage of relative renal function value.

After extracting one or more curve parameter values, the method proceeds to comparing the curve parameter value with a corresponding control curve parameter value. The control curve parameter value is obtained from an animal. A statistically significant change in the curve parameter value when compared to the control curve parameter value indicates change in renal function.

Another example of the current invention is a system for evaluating renal function of a live subject comprising intravenous administration of nanoparticles of a noble metal to the kidney of the subject, illumination of the kidney with a near infrared excitation wavelength such that the nanoparticles in the kidney fluoresces, and detection of presence or absence of nanoparticle fluorescence in the kidney of the live subject, wherein detection includes obtaining at least one image of the kidney through the subject's skin.

According to an embodiment of the invention, the noble metal may be selected from a group consisting of gold, silver, copper, platinum, palladium, or combinations thereof. The nanoparticles may have a hydrodynamic diameter less than 10 nm, possibly between 1 and 6 nm, or between 2 nm and 4 nm. According to another embodiment of the invention, the live subject may be a non-human mammal, such as a mouse. The nanoparticles may also have a core diameter less than 6 nm, possibly between 1 nm and 4 nm. The nanoparticles may be administered intravenously and may fluoresce in a near infrared emission wavelength. The nanoparticles may be coated with ligands such as glutathione, thiol-functionalized polyethylene glycol, cysteamine, cysteine, homocysteine, dipeptides containing cysteine (such as cysteine-glycine, cysteine-glutamic acid). The ligands may also be dipeptides (such as homocysteine-glycine and homocysteine-glutamic acid), tripeptides, and combinations of the two or more of the ligands listed herein.

According to another embodiment of the invention, the image of the kidney may be exhibited on a digital display. Taking at least one image of the kidney may involve taking sequential images within an evaluation time window, which may span 24 or fewer hours after administering the nanoparticles. In exemplary embodiments of the invention, the length of the evaluation time window may be between 1 second and 10 hours, possibly between 0.5 min and 3 hours or between 0.5 min and 60 min. The length of the evaluation of the evaluation time window may also be between 5 min and 10 hours, possibly between 10 min and 3 hours or between 20 min and 60 min.

Another example of the current invention is a kit comprising: an amount of nanoparticles of a noble metal in a sealed container. The amount of the nanoparticles is suitable for imaging kidneys of a mammal. The instructions include intravenous administering nanoparticles of a noble metal to a kidney of the live subject, illuminating the kidney with a near infrared excitation wavelength such that the nanoparticles in the kidney fluoresces, and detecting presence or absence of nanoparticle fluorescence in the kidney of the live subject. The noble metal may be selected from a group consisting of gold, silver, copper, platinum, palladium, or combinations thereof. Detecting presence or absence of nanoparticle fluorescence may involve obtaining at least one image of the kidney through the subject's skin. Taking at least one image of the kidney includes taking sequential images and the sequential images are collected at time intervals within an evaluation time window.

Current fluorescent contrast agents do not function like radiotracers, hampering their use in noninvasive kidney functional imaging. A commonly cited disadvantage is the limited penetration depth of the light. However, the failure of conventional organic fluorophores in noninvasive kidney functional imaging is not due to limited penetration depth of the light but their rapid accumulation and long retention in background skin tissues. This long-term challenge can be readily addressed with a renal clearable inorganic nanofluorophore, NIR-emitting glutathione-coated gold nanoparticles (GS-AuNPs), which integrates deep tissue-penetration of NIR light with desired in vivo behaviors into a synergy for high-contrast noninvasive kidney functional imaging. With NIR-emitting GS-AuNPs, contrast enhancement of the kidney increased 50-fold, and imaging time window is 1000 times greater than for conventional NIR organic fluorophores.

With the use of the GS-AuNPs and a mouse model for unilateral renal disease, the current invention demonstrates that fluorescence renograms derived from noninvasive fluorescence kidney imaging may be used to directly identify a kidney with impaired function and can differentiate dysfunction stages with manner consistent with histological evaluation of renal damage level.

EXAMPLES

The following experimental methods and characterization data were used for all compounds and their precursors exemplified herein.
Materials and Equipment.

Organic dyes disulfo-Cy3 carboxylic acid (Cy3) and disulfo-Cy7 carboxylic acid (Cy7) were purchased from Cyandye (Sunny Isles Beach, Fla., USA); IRDye 800CW, a cyanine dye, was purchased from Li-COR Biosciences (Lincoln, Nebr., USA). Hydrogen tetrachloroaurate ($HAuCl_4$) was purchased from Fisher Scientific (Waltham, USA). All the other chemicals mentioned in these Examples were purchased from Sigma-Aldrich and used as received.

FIG. 1A shows the chemical structures of two commonly-used organic dyes, disulfo-Cy3 carboxylate (Cy3) and disulfo-Cy7 carboxylate (Cy7), highlighting the increase of conjugation length from Cy3 to Cy7. The structure of IRDye 800CW is shown in FIG. 15.

Absorption spectra were collected using a Varian 50 Bio UV-Vis spectrophotometer. Luminescence spectra were collected by a PTI QuantaMaster™ 30 Fluorescence Spectrophotometer (Birmingham, N.J., USA). In vivo NIR fluorescence imaging was performed using a Carestream Molecular imaging system In-Vivo FX PRO (Billerica, Mass., USA).

Figure 1B:
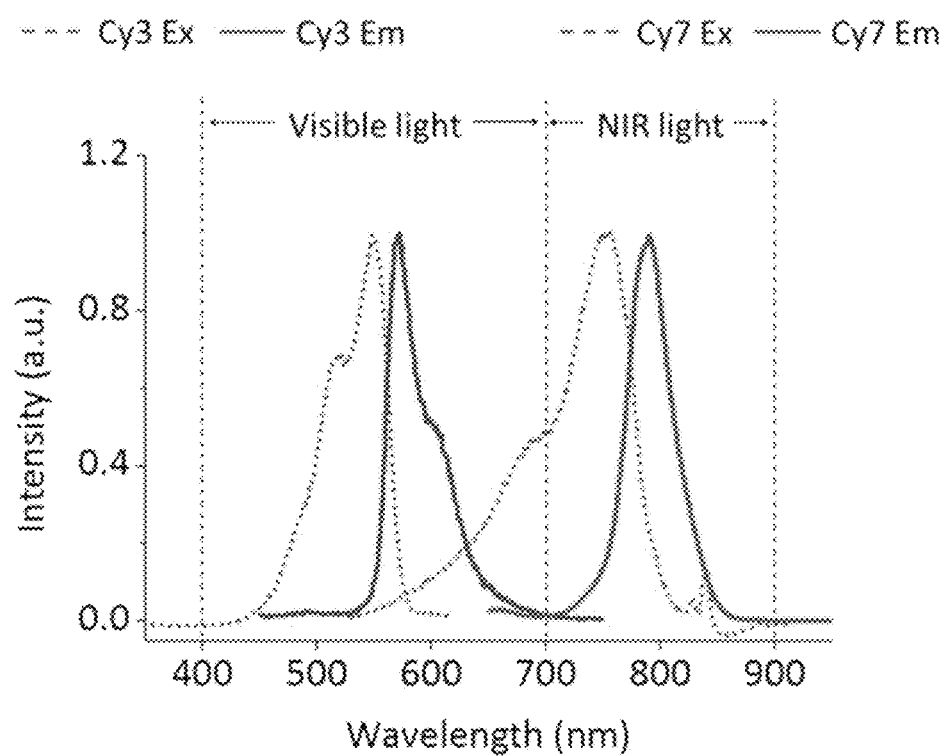
FIG. 1B shows the excitation and emission (Ex/Em) spectra of the organic dyes, Cy3 and Cy7. The increase in conjugation length from Cy3 to Cy7 corresponds to a shift in Ex/Em maxima from the visible region (Cy3, 550/570 nm) to the near infrared (NIR) optical window (Cy7, 754/790 nm).

FIG. 1B shows the excitation and emission (Ex/Em) spectra of the organic dyes, Cy3 and Cy7. The increase in conjugation length from Cy3 to Cy7 corresponds to a shift in Ex/Em maxima from the visible region (Cy3, 550/570 nm) to the near infrared (NIR) optical window (Cy7, 754/790 nm).
Synthesis of Noble Metal Nanoparticles: GS-AuNPs, GS-AgNPs, and GS-AuAgNPs.

Near IR emitting GS-AuNPs were synthesized according to the following protocol: 150 μL of 1 M HAuCl4 solution was added to 50 mL of 2.4 mM glutathione solution in a 100 ml three-necked flask while stirring vigorously. The mixture was then heated with an oil bath at 90° C. for 35 min. The resulting solution was cooled to room temperature and centrifuged at 21,000 g for 1 min to remove large aggregates. The NPs were precipitated out of the supernatant using the following steps: adding 1 M NaOH to the supernatant to adjust the pH to approximately 3; adding ethanol solution (2:1, $V_{water}/V_{ethanol}$); and centrifuging at 4,000 g for 5 min. The precipitates were suspended in 300 μL PBS buffer, and 1 M NaOH was added to adjust the pH to approximately 7. The PBS solution was centrifuged at 21,000 g for 1 min. The supernatant was the final product. For the animal studies, the GS-AuNPs were further purified using a NAP-5 column (Sephadex G-25 DNA Grade gravity columns) in phosphate buffer saline (PBS). The protocol to synthesize NIR-emitting GS-AuNPs is more completely described in Liu 2013, which is incorporated herein by reference. The complete citation for Liu 2013 is as follows: Liu, J., Yu, M., Zhou, C., Yang, S., Ning, X. & Zheng, J. Passive Tumor Targeting of Renal-Clearable Luminescent Gold Nanoparticles: Long Tumor Retention and Fast Normal Tissue Clearance. Journal of the American Chemical Society 135, 4978-81 (2013).

GS-AgNPs were prepared as follows. Precursor solutions were prepared by dissolving the glutathione and $AgNO_3$ in 40 ml water in the molar ratio of 34:1, where the total metal ion concentration of the solution was 5 mM. The solution was then heated at 95° C. for 37 h in an oil bath. After purification (via precipitation and resuspension as described above), the NIR-emitting GS-AgNPs obtained exhibited a mean hydrodynamic diameter (HD) of ~3.1 nm (assuming a normal distribution).

Synthesis of GS-Au/AgNPs may be accomplished using a co-reduction method. $HAuCl_4$ and $AgNO_3$ solutions are mixed in certain ratios, followed by chemical reduction with fresh prepared $NaBH_4$ solution (0.5M) in the presence of glutathione (GSH) in 4 mL distilled water at room temperature. After purification, glutathione coated Au/AgNPs (GS-Au/AgNPs) exhibiting 2.6±0.2 nm core diameter with 3.1±0.3 nm hydrodynamic diameter (HD) were obtained.

Figure 2A:
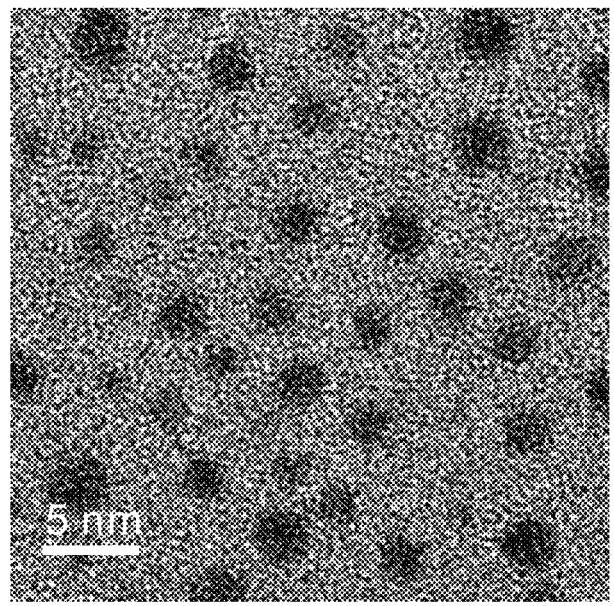
FIG. 2A shows a transmission electron microscopy (TEM) image of glutathione-coated Au—Ag alloy nanoparticles (GS-Au/AgNPs).
Figure 2B:
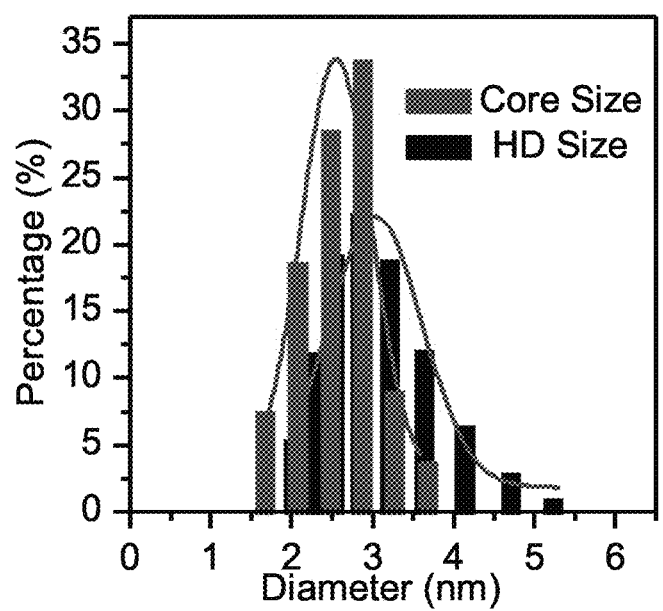
FIG. 2B shows the core size distribution for the GS-Au/AgNPs obtained from the TEM image of FIG. 2A and the hydrodynamic diameter (HD) distribution of the nanoparticles in aqueous solution measured via dynamic light scattering analysis.
Figure 2C:
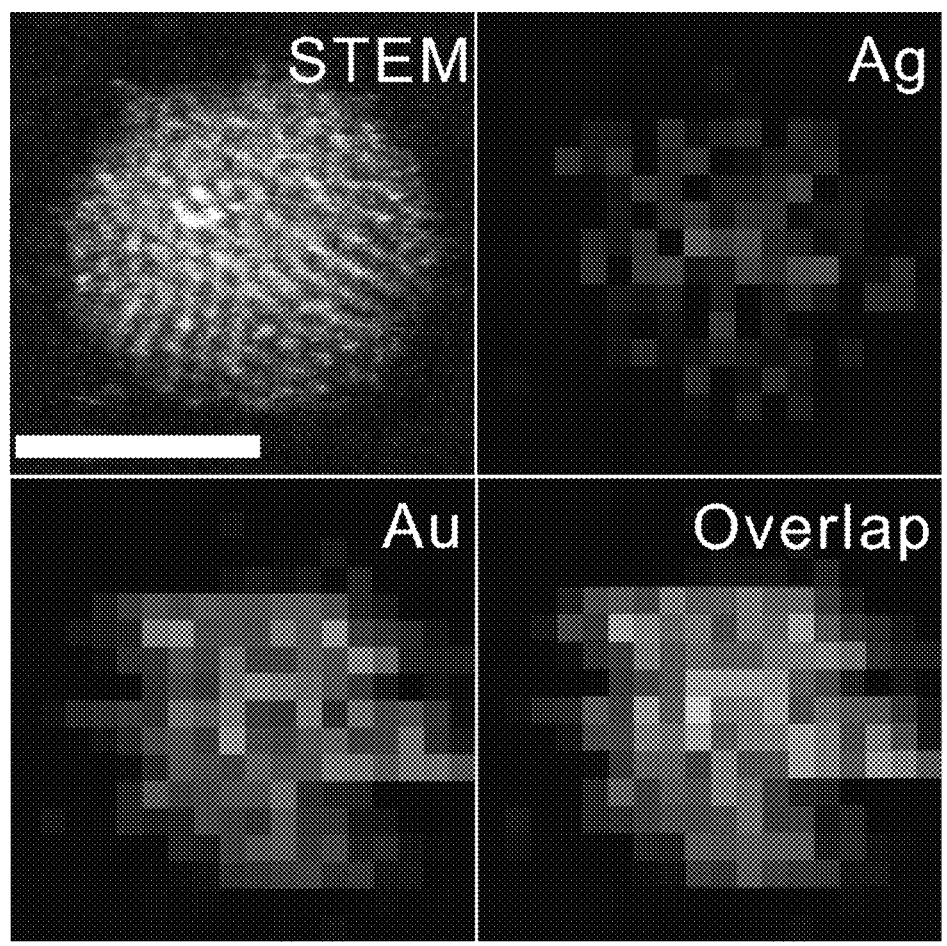
FIG. 2C shows scanning transmission election microscopy (STEM) and energy-dispersive X-ray spectroscopy (EDS) mapping images of the glutathione-coated gold/silver nanoparticles (GS-Au/AgNPs), which had an Au/Ag molar ratio of 1.4. (scale bar=2 nm)

FIGS. 2A-2C show results from characterization of glutathione-coated Au—Ag alloy nanoparticles (GS-Au/Ag-NPs). FIG. 2A shows a transmission electron microscopy (TEM) image of GS-Au/AgNPs. FIG. 2B shows the core size distribution (mean=2.6 nm, s.d.±0.2 nm, assumes Gaussian distribution) for the GS-Au/AgNPs obtain from the TEM image of FIG. 2A and the hydrodynamic diameter (HD) (mean=3.1 nm, s.d.±0.3 nm, assumes Gaussian distribution) of the nanoparticles in aqueous solution measured via dynamic light scattering analysis. FIG. 2C shows STEM and EDX mapping images of the GS-Au/AgNPs, which had an Au/Ag molar ratio of 1.4. (scale bar=2 nm)

In addition, scanning TEM (STEM) imaging coupled with energy-dispersive X-ray spectroscopy (EDS) further confirmed the successful synthesis of the hybrid GS-Au/AgNPs. As shown in FIG. 2C, elemental-mapping analysis indicates that all the Au and Ag atoms are homogeneously mixed within a single nanostructure, which is also supported by the result of the EDS point spectra of the individual particle. Here, two kinds of Au—Ag alloy NPs were prepared. These two Au—Ag nanoparticles are hereinafter referred to as GS-Au/Ag(1)NPs and GS-Au/Ag(2)NPs. The accurate Au/Ag atomic ratios of GS-Au/Ag(1)NPs and GS-Au/Ag(2)NPs were determined by ICP-MS, which are 10.6:89.4 and 60.6:39.4, respectively. These results suggest that the core densities of the two kinds of alloy metal NPs are 11.4 g/cm3 and 15.9 g/cm3 for GS-Au/Ag(1)NPs and GS-Au/Ag(2)NPs, respectively.

Animals

Animal studies were performed according to the guidelines of the University of Texas System Institutional Animal Care and Use Committee. Balb/c mice were obtained from Harlan Laboratories. The animals were housed in ventilated cages under standard environmental conditions (23±1° C., 50±5% humidity and a 12/12-hour light/dark cycle) with free access to water and standard laboratory food.

To obtain unilateral urethral obstruction (UUO) mice, male Balb/c mice (6-8 weeks old, with about 20 g) were anesthetized with isoflurane. For each mouse, the left kidney was exposed an incision on the left flank, and the left ureter was obstructed completely near the renal pelvis using a nonabsorbable suture. For mice in the sham group, the left ureter was exposed using the same surgical procedure but ureter ligation was not performed. Female Balb/c mice (8-10 weeks old, weighing about 20 g) were used as normal (non-UUO) mice for other experiments, such as those shown in FIGS. 4-19. The hair on the Balb/c mice was removed using hair removal lotion at least 24 h before the imaging experiments.

Fluorescence Kidney Imaging

Invasive and noninvasive imaging of normal mice, UUO mice and sham mice were performed using the following protocol. The protocol for invasive and noninvasive imaging differed in only in that for invasive imaging, the mouse's kidneys are exposed via removal of the mouse's back skin. An example of a skin-removed mouse prepared for invasive imaging is shown in FIG. 3.

Figure 3:
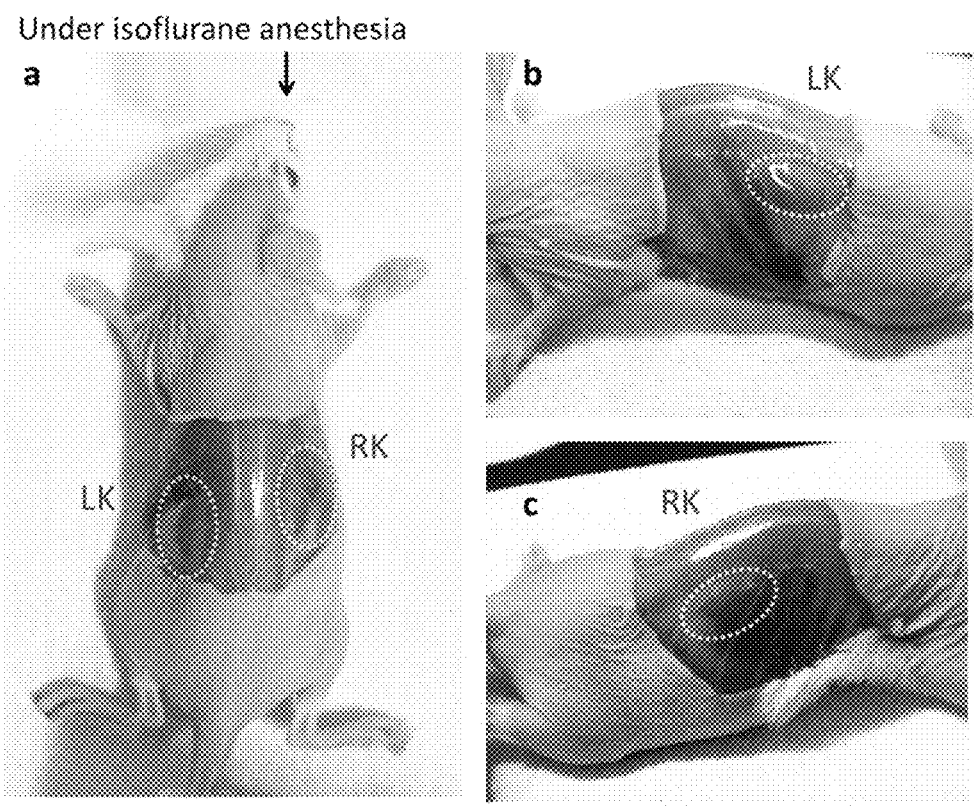
FIG. 3 shows a mouse after surgical removal of portions of its skin in order to expose its left kidney (LK) and right kidney (LK) for invasive imaging.

FIG. 3 shows a mouse after surgical removal of portions of its skin in order to expose its left kidney (LK) and right kidney (LK) for invasive imaging. As shown in panel a, the kidneys are paired bean-shaped organs lying on either side of the vertebral column. The right kidney (RK) of a mouse is usually slightly higher than it left kidney (LK). Since the kidneys locate retroperitoneally against the dorsal body wall, LK (shown in panel b) and RK (shown in panel c) can be exposed once the back skin above the kidneys was removed. The interference of skin on kidney imaging can be avoided in such an invasive way.

Prior to imaging, hair-removed Balb/c mice were anesthetized using 3% isoflurane. A catheter filled with PBS was inserted into each mouse's tail vein. The mouse, along with its tail vein catheter, was placed in supine position on the stage of fluorescence imaging system, with the mouse's back facing the excitation light and charge-coupled device (CCD) camera.

Fluorescence imaging of the each of mice proceeded as follows. Bright-field and fluorescence images of the each mouse was taken before injection with fluorophores. When its breathing rate decreased to 10-14 times per 15 s, the mouse was injected with 200 μL of a fluorophore solution. The fluorophore solutions used were PBS solutions of either an organic dye (Cy3, Cy7, or IRDye 800CW) or GS-AuNPs. The concentrations of Cy3, Cy7 and IRDye 800CW were 100, 10, and 10 μM, respectively, and these solutions were filtered through a 0.02 μm filter before injection. The solution of NIR-emitting GS-AuNPs contained 10 mg/mL gold atom as determined by inductively coupled plasma mass spectrometry (ICP-MS). Once the designated fluorophore solution was injected, whole body fluorescence images of each mouse were collected consecutively until 60 minutes post-injection. To ensure reproducible results, each mouse's anesthesia status was maintained at constant level before injection of fluorophores. Unlike clinical renographic procedures, no diuretic agents were used, and the animals were not hydrated prior to fluorescence imaging.

To study the long-term kidney visualization with GS-AuNPs, subsequent whole-body fluorescence imaging of UUO mice was also conducted at 2, 3, 4, 6, 8, 10, 12, 24 hours post-injection. Blood samples were collected for blood urea nitrogen (BUN) and serum creatinine (Scr) measurement.

Figure 4:
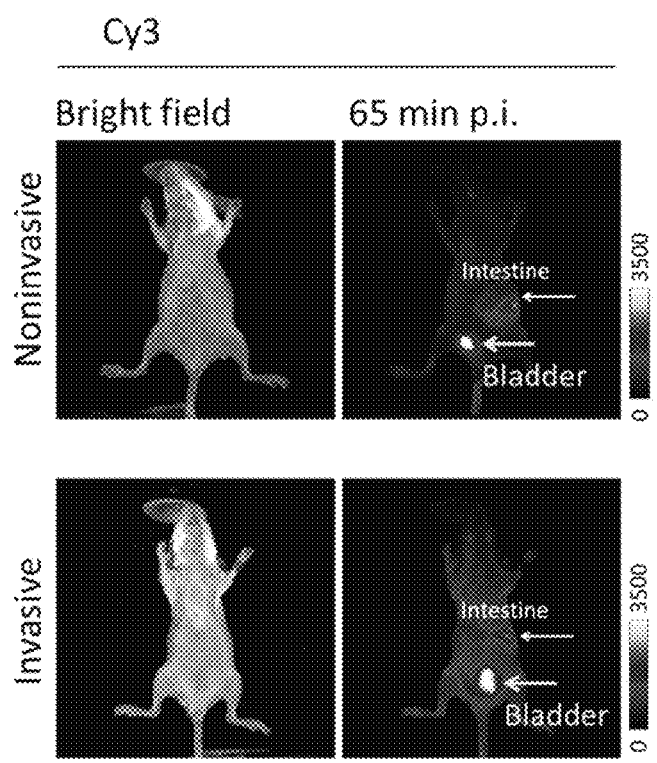
FIG. 4 shows bright field and fluorescence images of an intact mouse (via noninvasive imaging) and a skin-removed mouse (via invasive imaging), all taken approximately 65 minutes after injection with Cy3. The mice are in the prone position.
Figure 5:
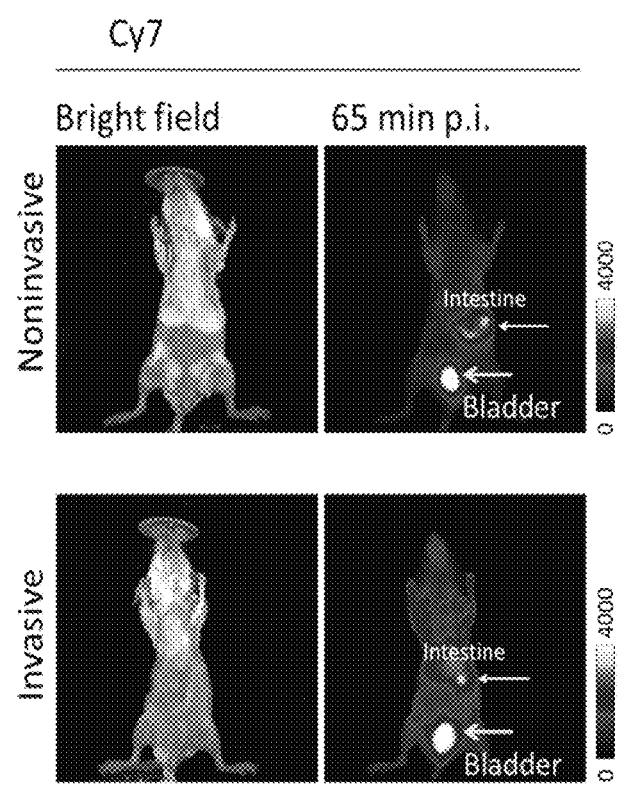
FIG. 5 shows bright field and fluorescence images of an intact mouse (via noninvasive imaging) and a skin-removed mouse (via invasive imaging), all taken approximately 65 minutes after injection with Cy7. The mice are in the prone position.
Figure 6:
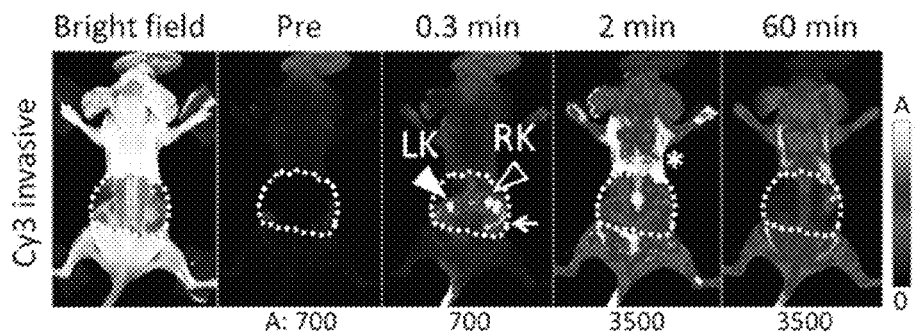
FIG. 6 shows bright field and whole-body fluorescence images of a skin-removed mouse, the latter using 550/600 nm (Ex/Em) filter sets. Invasive imaging was performed before and after Cy3 was intravenously injected. The bright field image was collected before Cy3 injection. Dashed white lines mark the area where the mouse's skin was removed in order to perform invasive imaging. The mice are in the supine position.
Figure 7:
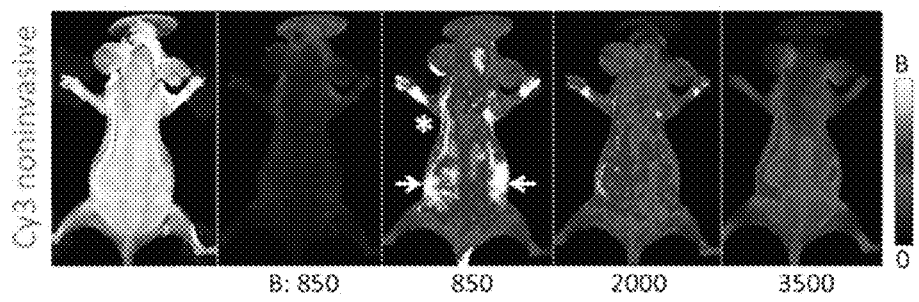
FIG. 7 shows bright field and whole-body fluorescence images of an intact mouse, the latter using 550/600 nm (Ex/Em) filter sets. Noninvasive imaging was performed before and after Cy3 was intravenously injected. The bright field image was collected before Cy3 injection. The mice are in the supine position.
Figure 8:
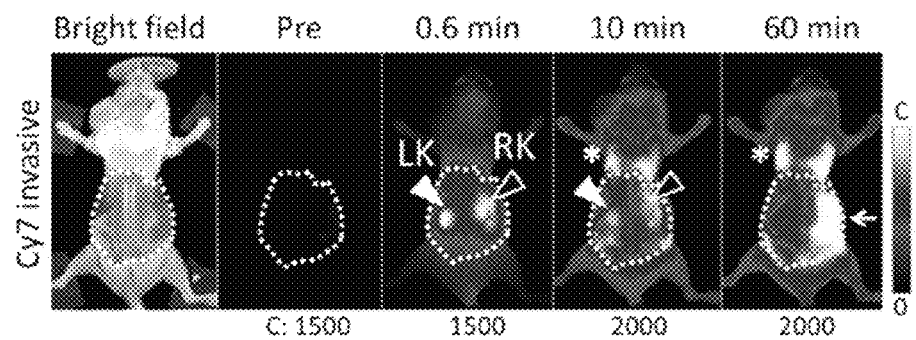
FIG. 8 shows bright field and whole-body fluorescence images of a skin-removed mouse, the latter using 710/790 nm (Ex/Em) filter sets. Invasive imaging was performed before and after Cy7 was intravenously injected. The bright field image was collected before Cy7 was injected. Dashed white lines mark the area where the mouse's skin was removed in order to perform invasive imaging. The mice are in the supine position.
Figure 9:
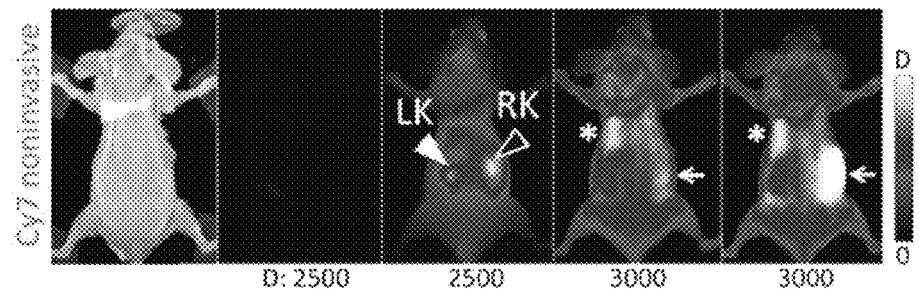
FIG. 9 shows whole-body fluorescence images of an intact mouse using 710/790 nm (Ex/Em) filter sets. Noninvasive imaging was performed before and after Cy7 was intravenously injected. The bright field image was collected before Cy7 was injected. The mice are in the supine position.
Figure 21:
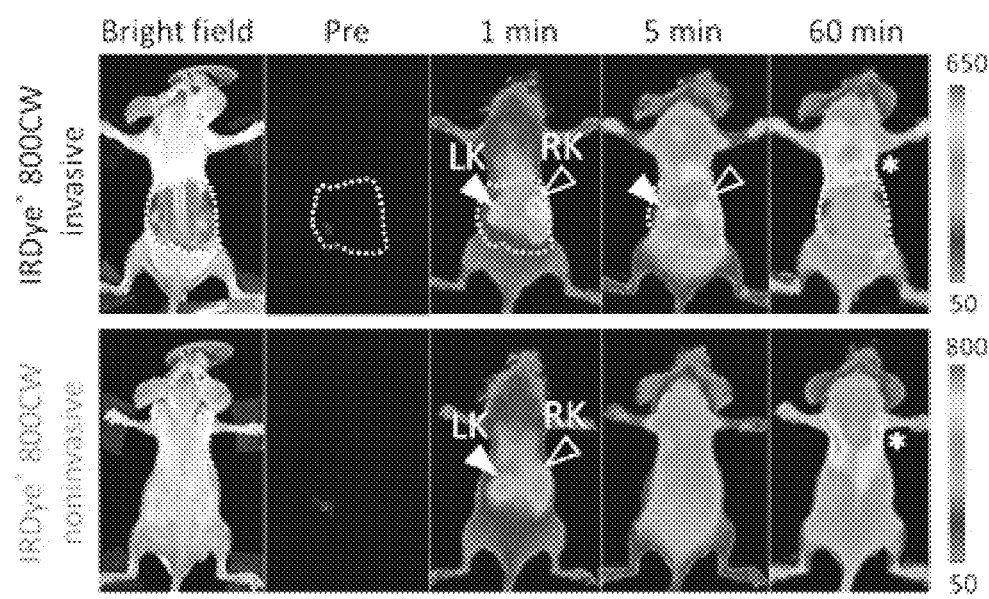
FIG. 21 shows bright field and fluorescence images of two different mice injected intravenously with IRDye 800CW carboxylate (Ex/Em filters: 710/790 nm). These fluorescence images were taken using invasive and noninvasive techniques before IRDye 800CW carboxylate was injected (Pre) and at 1 min, 5 min, and 60 min post injection. The bright field images were collected before dye was injected. Dashed white lines mark the area where the mouse's skin was removed in order to perform invasive imaging.
Figure 24:
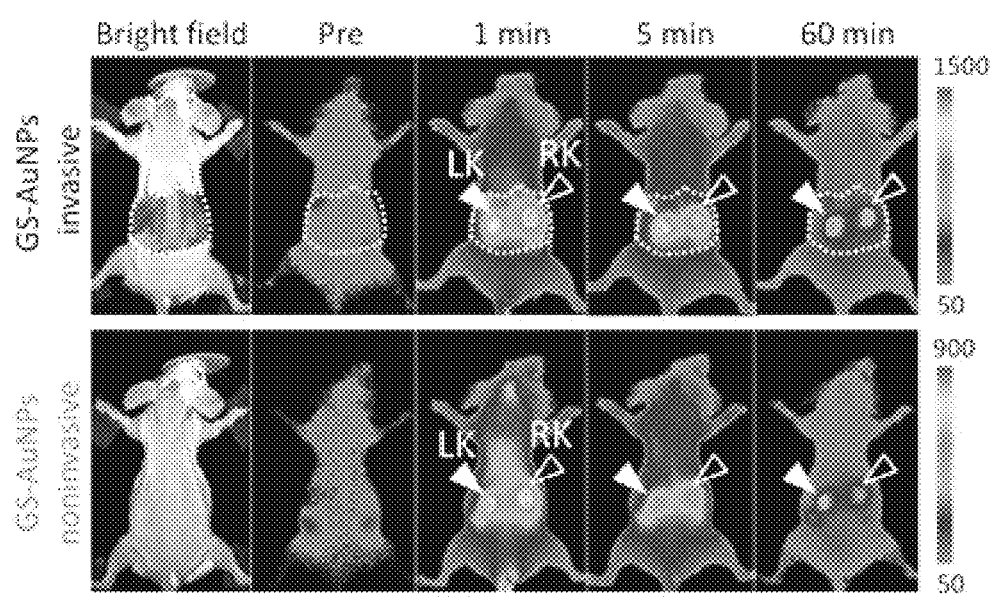
FIG. 24 shows bright field and fluorescence images of a skin-removed mouse (for invasive fluorescence imaging) and an intact mouse (for noninvasive fluorescence imaging) before and after intravenous injection with NIR-emitting GS-AuNP contrast dye (Ex/Em filters: 710/830 The bright-field images were collected before GS-AuNPs were injected. Dashed white lines mark the area where the mouse's skin was removed in order to perform invasive imaging.
Figure 36:
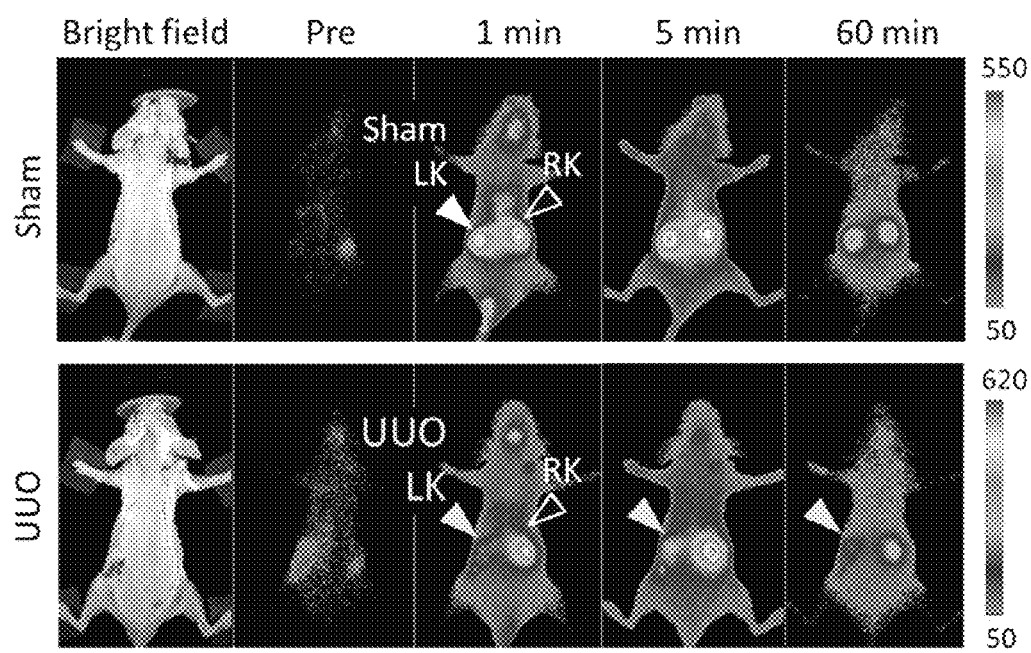
FIGS. 36-45 compare noninvasive fluorescence imaging of a unilateral ureter obstruction (UUO) mouse and a sham control mouse after intravenous injection of GS-AuNPs. The UUO mice were generated by ligation of the left ureter while the right ureter was kept intact.
Figure 54:
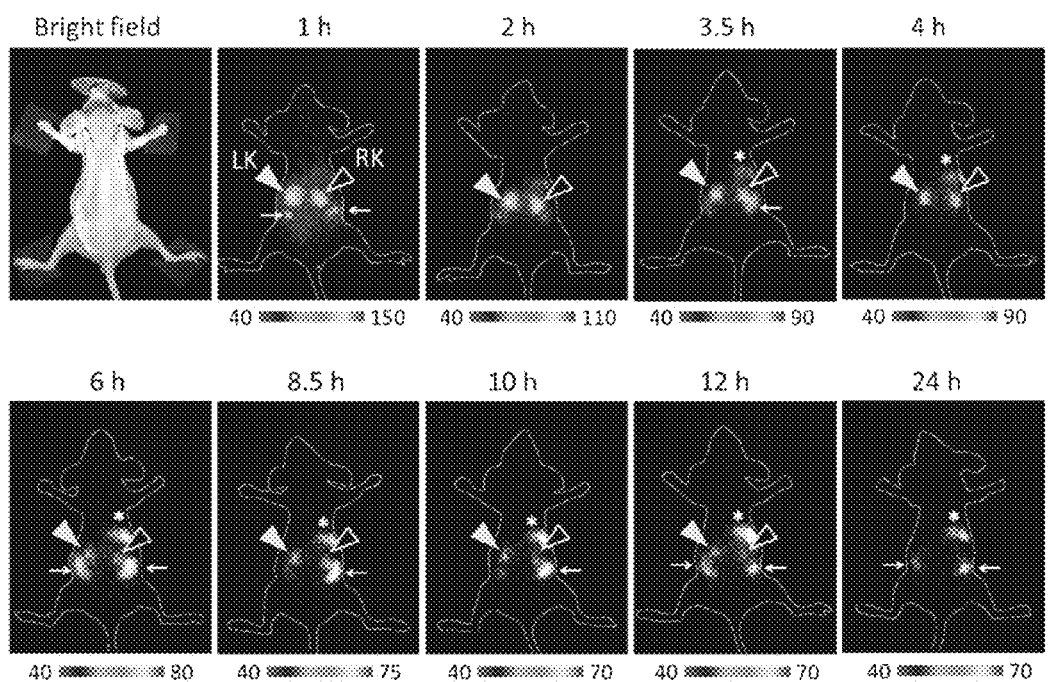
FIG. 54 shows fluorescence images of a mouse injected with NIR-emitting GS-AuNPs (Ex/Em filters: 710/830 nm) taken using noninvasive techniques at various time points in the 24-hour time span after intravenous injection.

The parameters for acquiring the fluorescence images were shown as follows: Cy3, excitation at 550/10 nm, emission at 600/20 nm, exposure time of 2 s, no binning (FIGS. 4, 6, and 7); Cy7, excitation of 710/10 nm, emission of 790/20 nm, exposure time of 5 s, 2×2 binning (FIGS. 5, 8, and 9); IRDye 800CW, excitation of 710/10 nm, emission of 790/20 nm, 2×2 binning, exposure time of 5 s (FIGS. 21 and 55); GS-AuNPs, excitation of 710/10 nm, emission of 830/20 nm; exposure time of 30 s, 2×2 binning (FIGS. 24, 36, and 54).

Image Analysis

Regions of interest (ROIs) designated "kidney areas" were defined around the left and right kidneys on the fluorescence image showing high kidney intensity. Four ROIs designated "surrounding tissue areas" were drawn in proximity to the each kidney; the mean values of these four ROIs were considered the "mean intensity of surrounding tissue area" for the respective kidney. The percentage of kidney contrast enhancement was calculated as follows:

$$\text{Percentage Kidney contrast enhancement} = \left[\frac{\text{mean intensity of kidney}}{\text{mean intensity of surrounding tissue}} - 1\right] \times 100\%$$

Figure 10:
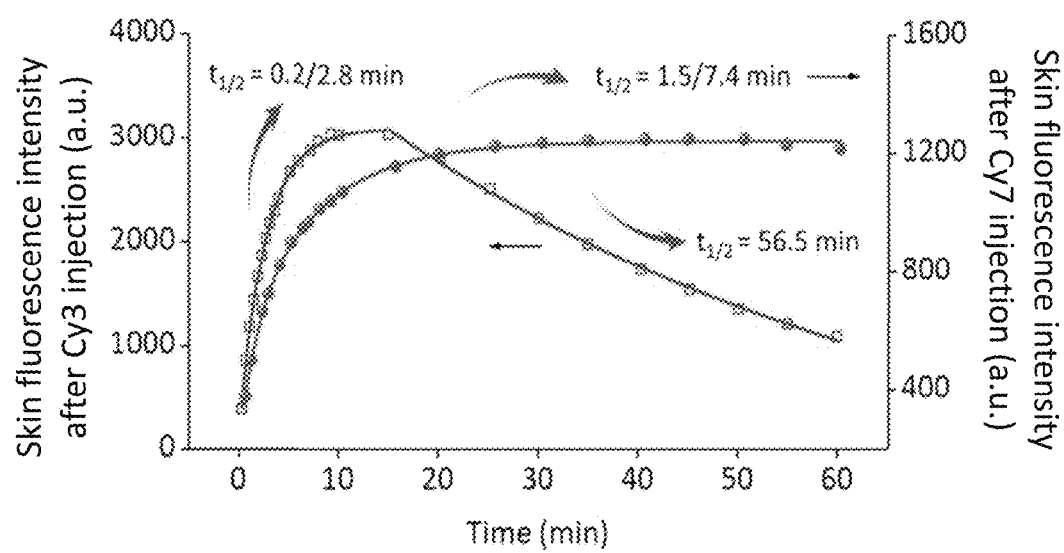
FIG. 10 shows the fluorescence intensity of mice skins following injection with Cy3 (squares) and Cy7 (circles). Data was collected using fluorescence imaging techniques.
Figure 22:
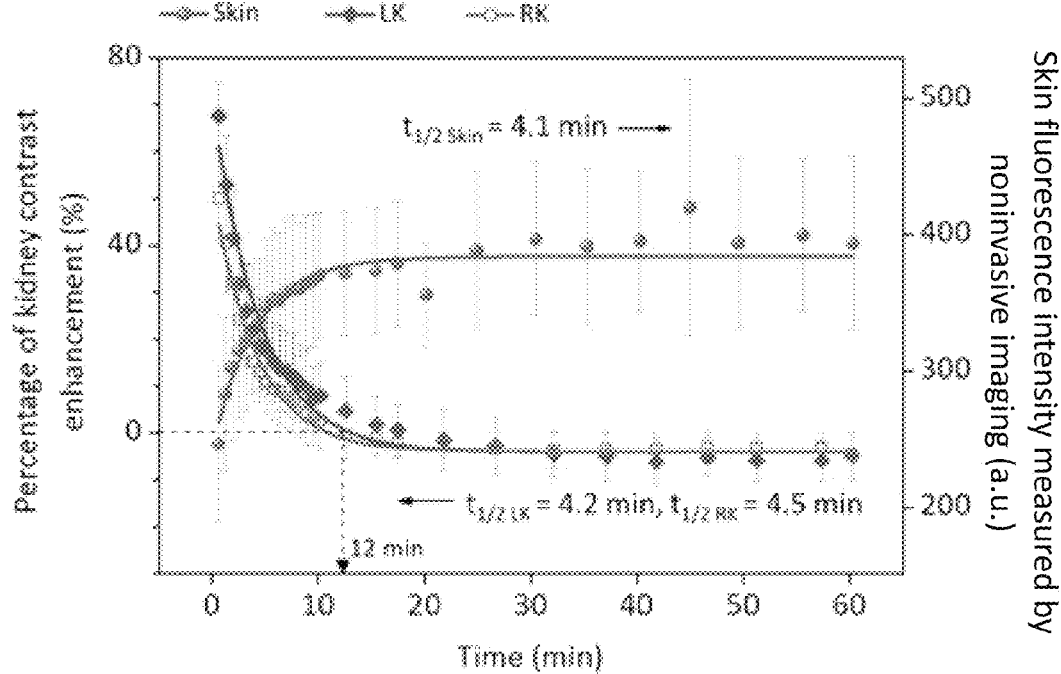
FIG. 22 shows changes in mouse skin fluorescence intensity and the percentage of contrast enhancement of mouse kidneys following IRDye 800CW injection and obtained via noninvasive imaging. N=3, mean±s.d.
Figure 23:
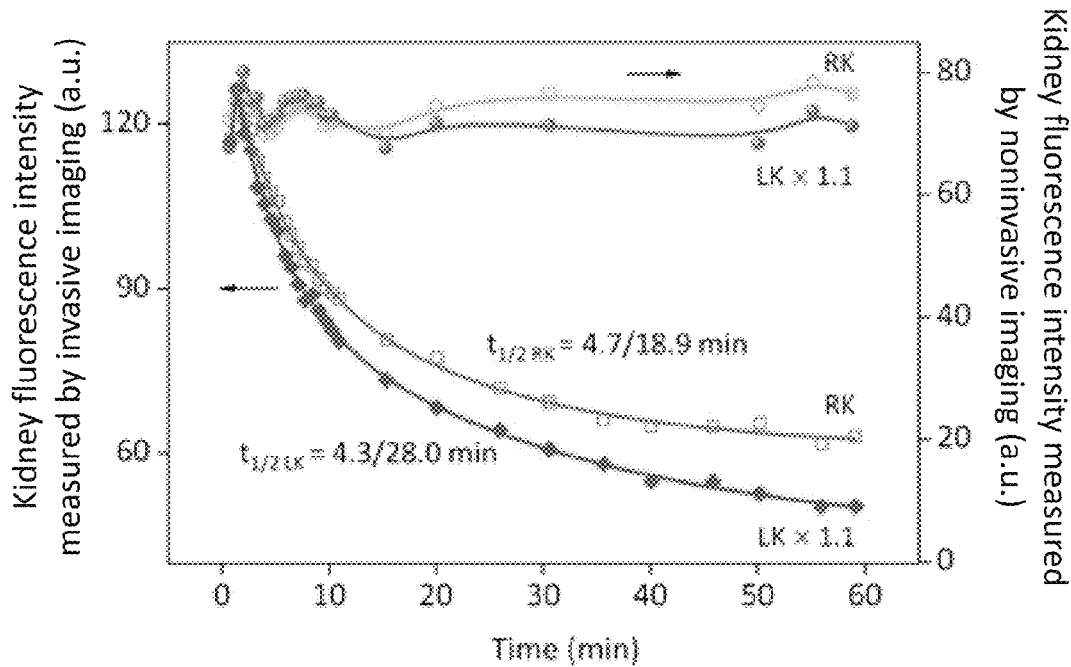
FIG. 23 shows changes in fluorescence intensity of the right kidney (RK) and left kidney (LK) of skin-removed (imaged invasively) and intact mice (imaged noninvasively) following IRDye 800CW injection.

For GS-AuNPs, the ROIs of "skin" were chosen from the back area close to the tail, so as to avoid the influence of bright kidneys. The time-dependent fluorescence intensity of skin (or kidneys) and percentage of kidney contrast enhancement (FIGS. 10-14, 22, 23, 25, 26, 37, 56, and 57). The curves were fitted with exponential functions to generate the kinetics of kidney contrast change or the kinetics of accumulation and clearance of the fluorophores in the skin and kidneys (FIGS. 10, 22, and 23). Deconvolution and parametric analysis of the kidney TFICs were performed using Origin 8 (FIGS. 27-35; Tables 1 and 2).

Pathological Analysis

Kidneys were removed from euthanized mice, fixed in 10% buffered formalin for paraffin embedding, and then sectioned into 5-µm sections. The tissue sections were stained with hematoxylin-eosin (HE) and subjected to blind histopathologic evaluation (FIGS. 47-49 and 51-53).

Limitations of Current Organic Dyes in Noninvasive Kidney Imaging

Although the failure of fluorescence techniques in noninvasive kidney imaging is often attributed to the limited tissue penetration of the light, a comparison of two organic dyes with distinct excitation and emission wavelengths in kidney imaging revealed that light penetration depth is not the only factor that governs kidney-contrast enhancement and imaging time window.

FIGS. 4 and 5 show noninvasive and invasive fluorescence imaging of mice after intravenous (i.v.) injection of two renal clearable Cyanine dyes, Cy3 and Cy7, respectively. Noninvasive imaging requires mere hair removal, producing a nude but intact mouse. On the other hand, invasive imaging requires an additional step—removing some of the skin on the mouse's back in order to expose the kidneys. Examples of skin-removed mice are shown FIG. 3.

FIG. 4 shows bright field and fluorescence images of an intact mouse (for noninvasive imaging) and a skin-removed mouse (for invasive imaging), taken 65 minutes after injection with Cy3. The mouse is shown in the prone position. Strong fluorescence is detected from bladder, indicating Cy3 can be excreted into urine through renal clearance.

FIG. 5 shows bright field and fluorescence images of an intact mouse (for noninvasive imaging) and a skin-removed mouse (for invasive imaging), taken 65 minutes after injection with Cy7. The mouse is in the prone position. Strong fluorescence is detected from bladder, indicating Cy7 can be excreted into urine through renal clearance.

Whole-body fluorescence images of mice were also obtained immediately after intravenous injection with Cy3 (FIGS. 6 and 7) and Cy7 (FIGS. 8 and 9). In these images, the mice were in the supine position.

FIG. 6 shows bright field and whole-body fluorescence images of a skin-removed mouse, the latter using 550/600 nm (Ex/Em) filter sets. Invasive imaging was performed before Cy3 was intravenously injected and at 0.3 min, 2 min, and 60 min after injection. The bright field image was collected before Cy3 injection. Dashed white lines mark the area where the mouse's skin was removed in order to perform invasive imaging. LK and RK denote to the left and right kidneys, respectively. The mice are in the supine position.

FIG. 7 shows bright field and whole-body fluorescence images of an intact mouse using, the latter using 550/600 nm (Ex/Em) filter sets. Noninvasive imaging was performed before Cy3 was intravenously injected and at 0.3 min, 2 min, and 60 min after injection. The bright field image was collected before Cy3 injection. The mice are in the supine position.

FIG. 8 shows bright field and whole-body fluorescence images of a skin-removed mouse, the latter using 710/790 nm (Ex/Em) filter sets. Invasive imaging was performed before Cy7 was intravenously injected and at 0.6 min, 10 min, and 60 min after injection. The bright field image was collected before Cy7 was injected. Dashed white lines mark the area where the mouse's skin was removed in order to perform invasive imaging. LK and RK denote to the left and right kidneys, respectively. The mice are in the supine position.

FIG. 9 shows bright field and whole-body fluorescence images of an intact mouse, the latter using 710/790 nm (Ex/Em) filter sets. Noninvasive imaging was performed before Cy7 was intravenously injected and at 0.6 min, 10 min, and 60 min after injection. The bright field image was collected before Cy7 was injected. LK and RK denote to the left and right kidneys, respectively. The mice are in the supine position.

While both Cy3 and Cy7 rapidly accumulated in the kidneys within 1 minute post-injection (p.i.) as shown in invasive imaging (when the kidneys are surgically exposed, FIGS. 1, 6, and 8), Cy3 failed to enhance contrast for the noninvasively imaged mouse kidney (FIG. 7). Furthermore, the NIR-emitting Cy7 was able to improve contrast for the noninvasively imaged mouse kidney for less than 10 minutes (FIG. 9). At 10 min p.i., the kidneys of mice injected with Cy7 became undetectable to noninvasive imaging (FIG. 9) even though Cy7 remained in the kidneys, as shown in FIG. 8.

FIG. 10 shows the fluorescence intensity of mouse skins following injection of with Cy3 (squares) and Cy7 (circles). Cy3 and Cy7 both accumulated rapidly in the skins and were retained long periods of time. Compared with the visible dye Cy3, the NIR dye Cy7 was retained in the skin for a longer period of time.

Figure 11:
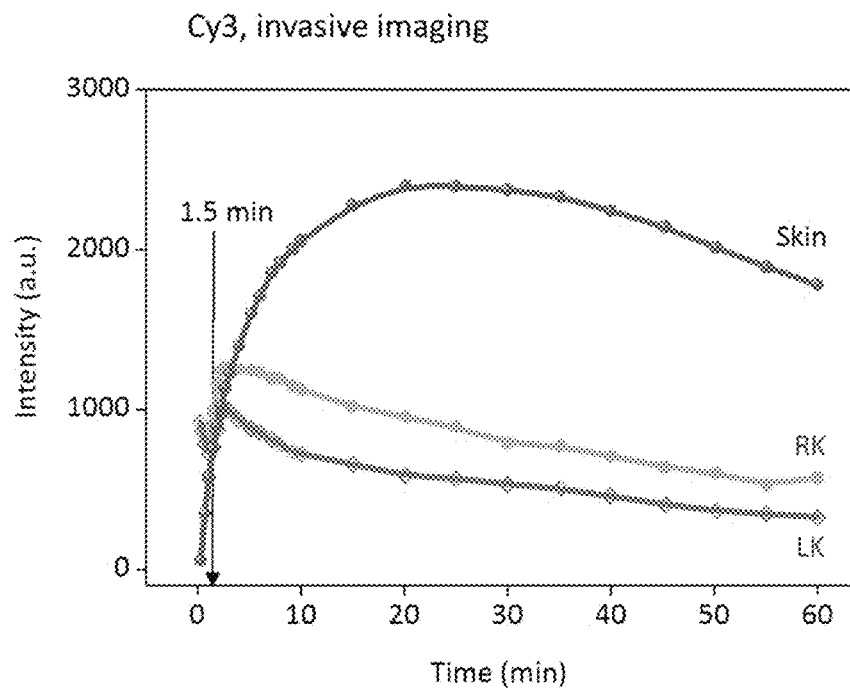
FIG. 11 shows time-fluorescence intensity curves (TFICs) of the skin, right kidney (RK), and left kidney (LK) of a skin-removed mouse, with invasive imaging performed immediately after Cy3 injection.

FIG. 11 shows time-fluorescence intensity curves (TFICs) of mouse skin and right and left kidneys (RK and LK, respectively) obtained from invasive imaging performed immediately after Cy3 injection. The data shown in FIG. 11 was obtained from the images such as those shown in FIG. 6. The same data set was used to generate the results in FIG. 11 and the images in FIG. 6.

Figure 12:
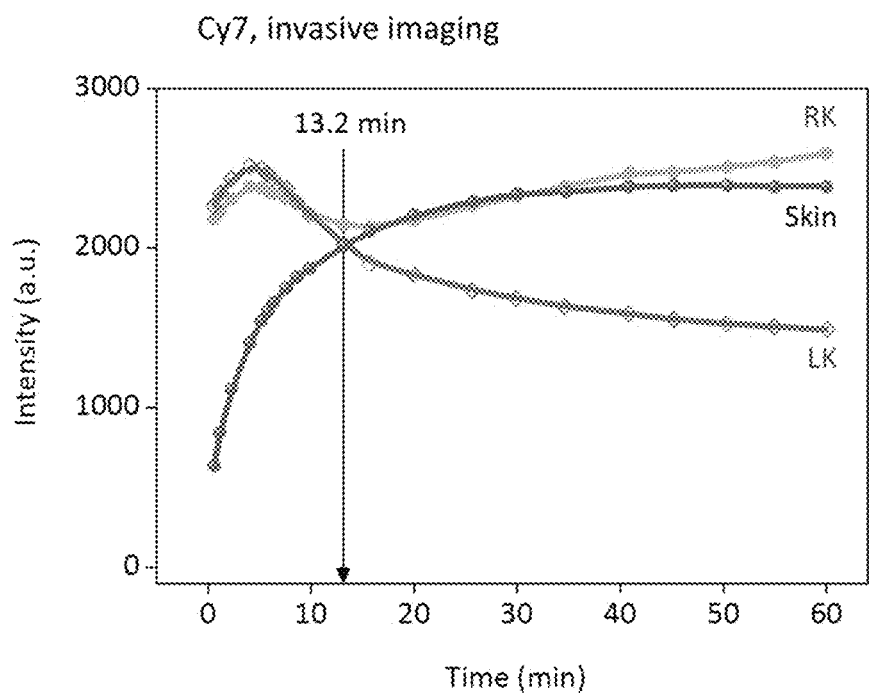
FIG. 12 shows time-fluorescence intensity curves (TFICs) of the skin, right kidney (RK), and left kidney (LK) of a skin-removed mouse, with invasive imaging performed immediately after Cy7 injection.

FIG. 12 shows time-fluorescence intensity curves (TFICs) of mouse skin and right and left kidneys (RK and LK, respectively) obtained from invasive imaging performed immediately after Cy7 injection. The same data set was used to generate the results in FIG. 12 and the images in FIG. 8.

When kidneys are surgically exposed as shown in FIG. 3, the fluorescence intensities of left kidney (LK) and right kidney (RK) can be directly detected and compared with intensity of surrounding skin tissue. The skins' fluorescence intensity values (skin intensity) were found to quickly surpass fluorescence intensities for both left and right kidneys, at 1.5 min p.i. for Cy3 (FIG. 11) and 13.2 min p.i. for Cy7 (FIG. 12). Besides renal clearance, Cy7 can also be excreted through a hepatic route, resulting in dramatic fluorescence enhancement of mouse intestines after 10 min p.i. (shown using arrows in FIGS. 8-9). In mice injected with Cy7, the close proximity of the intestine and the right kidney (RK) causes intestine signal to interfere with the RK signal, thus resulting in artificial increase of the RK signal after 13.2 min (FIG. 12) rather than gradual decrease, as seen in the LK signal.

Figure 13:
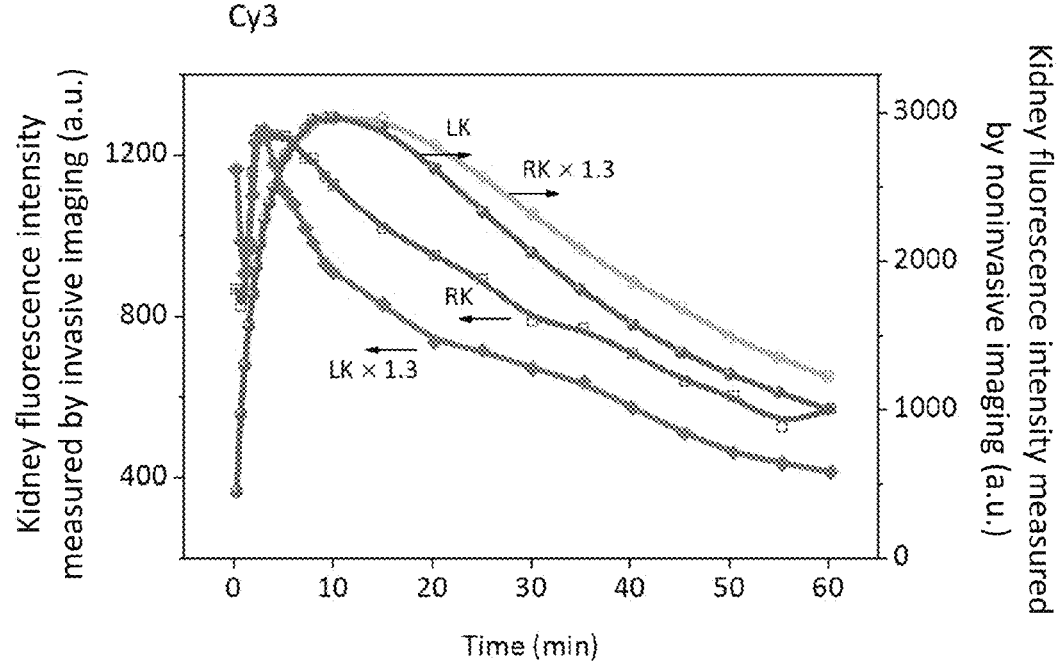
FIG. 13 shows a comparison on time-fluorescence intensity curves (TFICs) derived from noninvasive and invasive imaging after Cy3 and Cy7 injection.

FIG. 13 shows a comparison on time-fluorescence intensity curves (TFICs) derived from noninvasive and invasive imaging after Cy3 injection. FIG. 13 was generated from the same data set as FIGS. 6-7.

Figure 14:
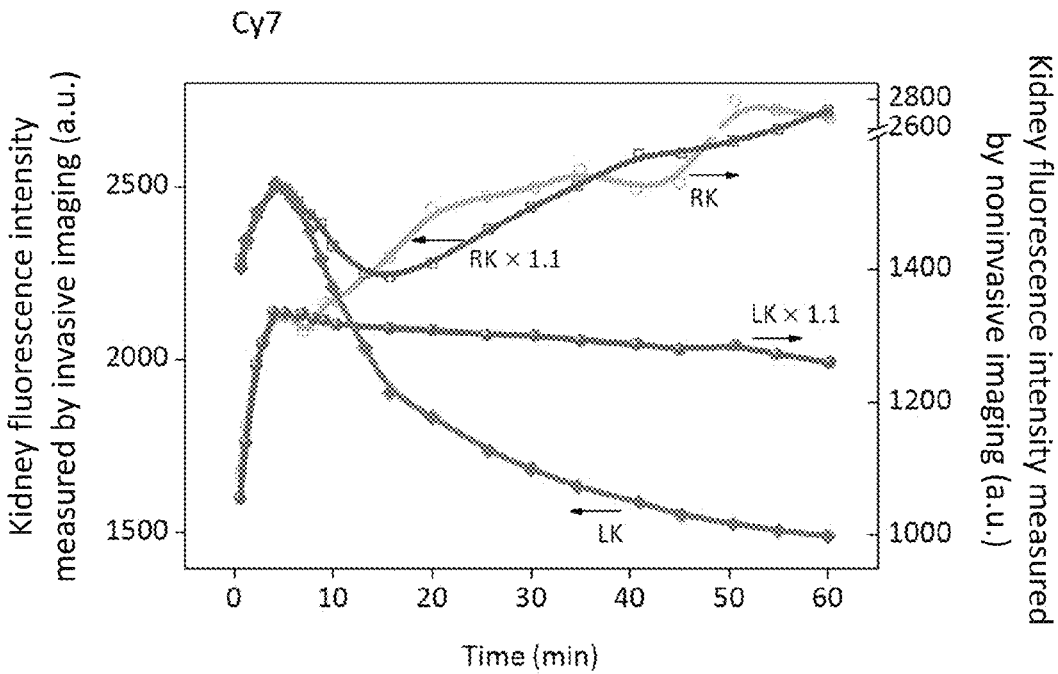
FIG. 14 shows a comparison on time-fluorescence intensity curves (TFICs) derived from noninvasive and invasive imaging after Cy7 injection.

FIG. 14 shows a comparison on time-fluorescence intensity curves (TFICs) derived from noninvasive and invasive imaging after Cy7 injection. FIG. 14 was generated from the same data set as FIGS. 8-9.

The noninvasive kidney TFICs utilizing Cy3 (FIG. 13) or Cy7 (FIG. 14) as contrast agents differed significantly from the curves generated via invasive imaging because noninvasive imaging using Cy3 and Cy7 suffered severe interference from skin fluorescence. Therefore, both Cy3 and Cy7 failed to report noninvasive renograms that adequately describe a dynamic process of probe clearance through kidney, key to kidney functional imaging. For Cy7 (FIG. 14), dramatic fluorescence enhancement of the intestine led to an increase of RK intensity after 10 min in both noninvasive and invasive imaging (squares and open circles).

The low contrast between kidney and skin fluorescence and short detection-time window of organic fluorophores (even with NIR excitation/emission) stems from rapid accumulation and long retention of the Cy3 and Cy7 dyes in the background skin tissues, which overwhelmed accumulation and clearance of the dyes from the kidneys. After intravenous injection of the Cy3 and Cy7 dyes, the skin fluorescence intensity (or skin intensity) increased dramatically, showing two-phase exponential growth kinetics (FIG. 10). In fact, the increase half-lives were only 0.2 min (18.1%)/2.8 min (81.9%) for Cy3 and 1.5 min (33.5%)/7.4 min (66.5%) for Cy7 (FIG. 10).

As previously mentioned, the skin fluorescence intensity surpassed kidney intensity at 1.5 min p.i. for Cy3 and at 13.2 min p.i. for Cy7 (FIGS. 11-12), indicating that the rapid disappearance of kidney in noninvasive images stemmed from the increasing skin background that quickly overwhelmed the kidney signal rather than insufficient tissue penetration of light or rapid clearance of the dyes from the kidneys. Cy3 skin clearance half-life was 56.5 min. for Cy3. However, Cy7 skin clearance half-life was prolonged: No clearance of Cy7 from the skin was observed during 60 min p.i. The extended n-conjugated system of the Cy7 NIR dye likely significantly increased its affinity to background tissues such as skin. This conclusion is consistent with observations made by other research groups (Choi 2013).

Such long-term retention of dye in the skin deters from the use of organic dyes as a renogram for elucidation of the dynamic clearance process of probes through kidney, key to kidney functional imaging (FIGS. 13-14). Consequently, design of organic fluorophores for noninvasive kidney functional imaging fell into a dilemma: while increasing conjugation length shifts the excitation and emission maxima of organic molecules from the visible region to NIR optical window, the large hydrophobic n-conjugated systems of NIR dyes lead to a high skin accumulation and thus generate a strong persistent fluorescence background, precluding NIR organic dyes from serving as contrast agents for noninvasive kidney functional imaging.

Comparison of Inorganic and Organic Renal Clearable Fluorophores in Noninvasive Dynamic Imaging of Kidney Unlike organic fluorophores for which the excitation and emission wavelengths strongly depend on hydrophobic n-conjugated systems, luminescent inorganic nanoparticles can exhibit NIR emissions due to quantum size effects without sacrificing their hydrophilicity. (Alivisatos 1996; Zheng 2007; Zheng 2012; Wilson 1993; Sun 2006; Vlasov 2014; Park 2009). Among those known inorganic nanoemitters, luminescent glutathione-coated AuNPs (GS-AuNPs) are a class of ultrasmall inorganic fluorphores that have hydrophilic surface (Zhou 2010; Yu 2011) and can also be effectively excreted into the urine through kidney with little accumulation in normal tissues and organs (Zhou 2011; Zhou 2012 and Liu 2013).

FIG. 15 shows the chemical structure of IRDye 800CW carboxylate and a schematic representation of NIR-emitting gold nanoparticles with glutathione-coated surfaces (GS-AuNP). The nanoparticles have a core size of about 2.5 nm and hydrodynamic diameter (HD) of about 3.3 nm.

Figure 16:
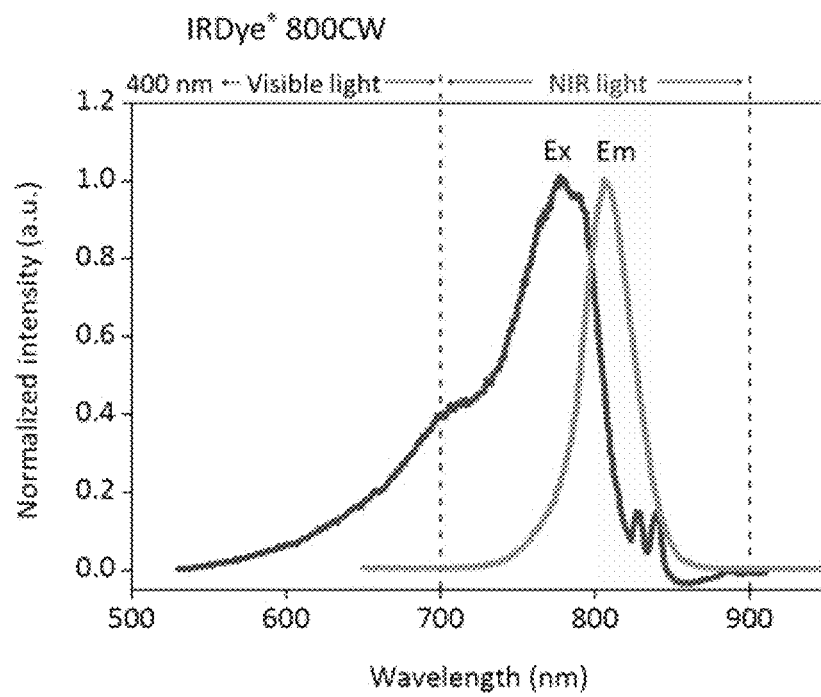
FIG. 16 shows the excitation (Ex) and emission (Em) spectra of IRDye 800CW carboxylate in phosphate buffer saline (PBS), measured using a fluorescence spectrophotometer. The excitation/emission maxima of IRDye 800CW in PBS is 779/806 nm.

FIG. 16 shows the near IR excitation (Ex) and emission (Em) spectra of IRDye 800CW. The excitation and emission maxima of IRDye 800CW are 779 nm and 806 nm, respectively.

Figure 17:
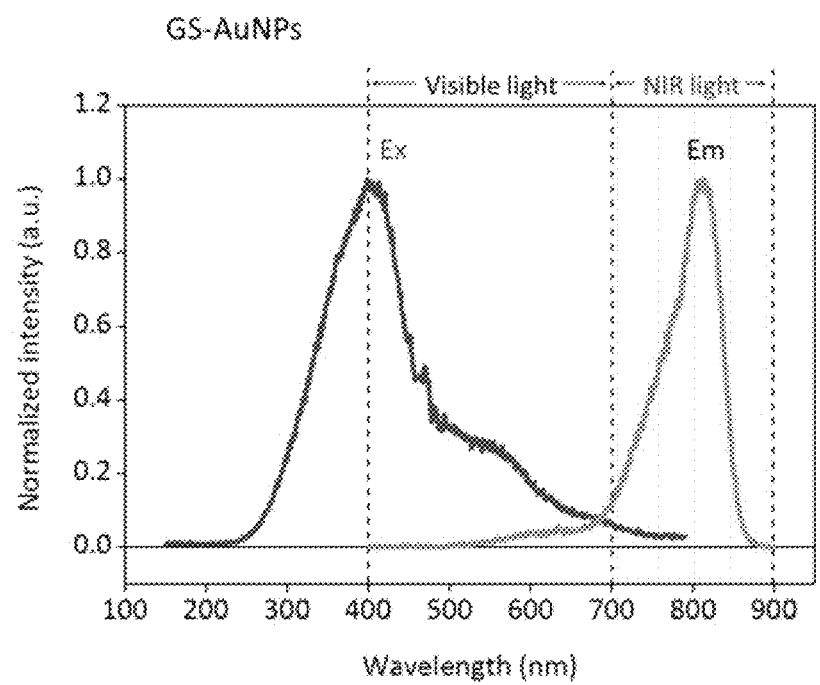
FIG. 17 shows the excitation (Ex) and emission (Em) spectra of GS-AuNPs in PBS, measured using a fluorescence spectrophotometer. The excitation/emission maxima of GS-AuNPs in PBS is 400/810 nm. The excitation spectrum of GS-AuNPs has a shoulder peak at 560 nm that extends to NIR region (700-900 nm), meaning the GS-AuNPs may be excited by NIR light.

FIG. 17 shows the near IR excitation and emission spectra of the GS-AuNPs. The excitation and emission maxima of GS-AuNPs are 400 nm and 810 nm, respectively. While the dominant excitation peak of the GS-AuNPs is located in the visible region, a shoulder in the excitation spectra (peak at around 560 nm) extends to NIR region (700-900 nm), enabling excitation of the GS-AuNPs by NIR light for use in an in vivo imaging system. This use is further demonstrated in FIGS. 19-20.

Figure 18:
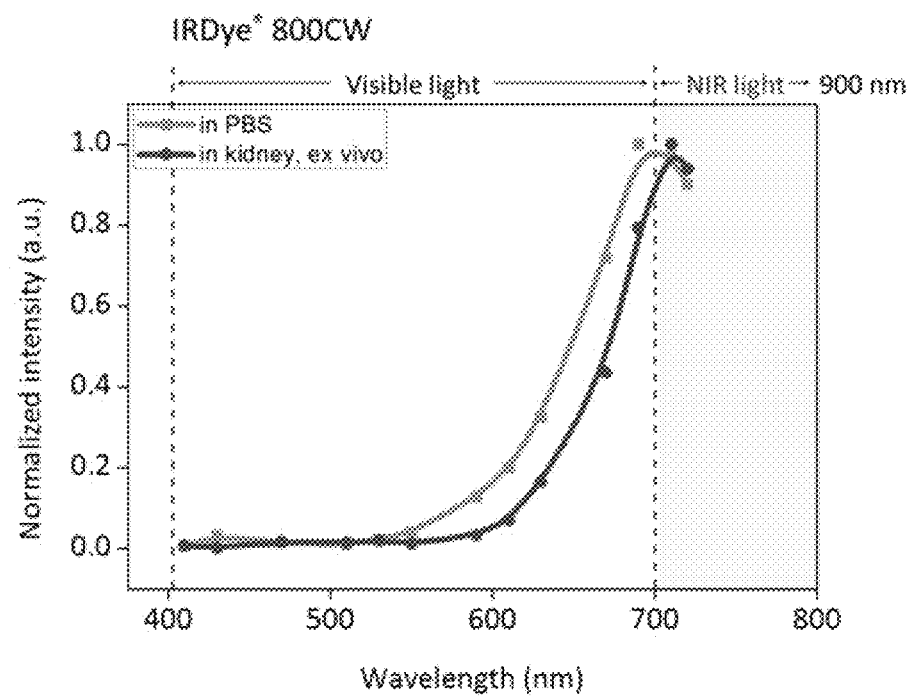
FIG. 18 displays the excitation spectra of IRDye 800CW measured using in vivo fluorescence imaging system. Shown are the spectra for IRDye 800CW in PBS and from dissected kidneys (30 min p.i., ex vivo imaging).
Figure 19:
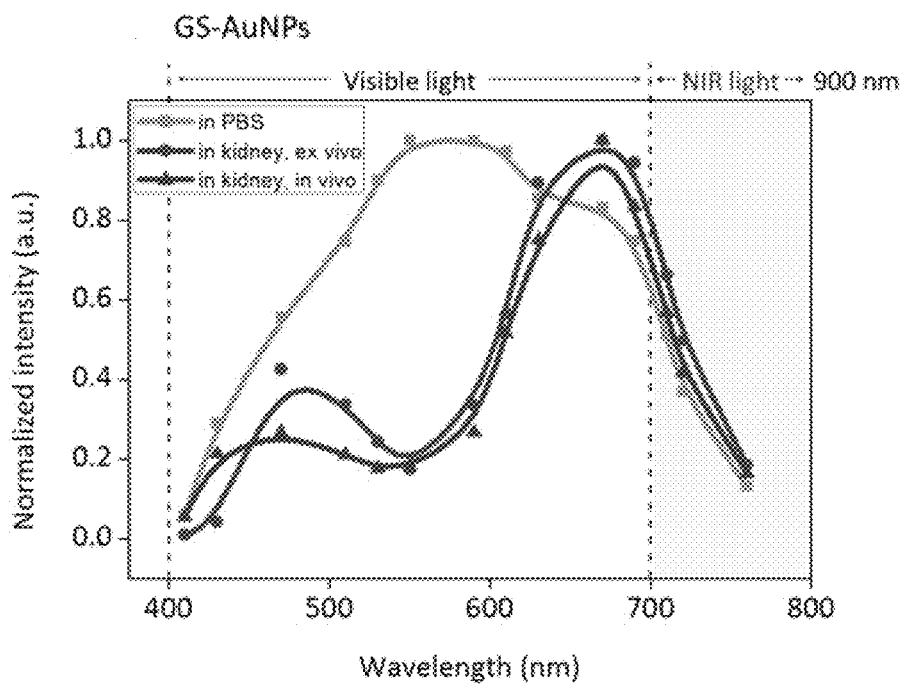
FIG. 19 displays the excitation spectra of GS-AuNPs measured using in vivo fluorescence imaging system. Shown are the spectra for GS-AuNPs in PBS, from dissected kidneys (30 min p.i., ex vivo imaging), and from the kidney area of a live mouse (30 min p.i., noninvasive in vivo imaging, only possible for GS-AuNPs).

FIGS. 18 and 19 display the excitation spectra of IRDye 800CW and GS-AuNPs, respectively. The spectra are measured using in vivo fluorescence imaging system in PBS, from dissected kidneys (30 min p.i., ex vivo imaging) and from kidney area of live mouse (30 min p.i., noninvasive in vivo imaging, only possible for GS-AuNPs).

Figure 20:
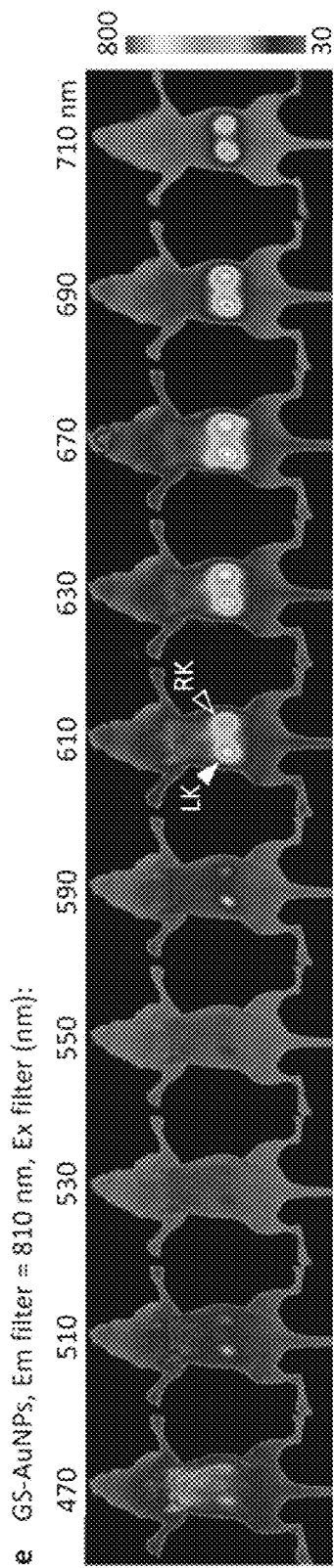
FIG. 20 shows the whole-body fluorescence images of a mouse 30 min after intravenous injection of GS-AuNPs, detected at different excitation wavelengths demonstrated that the kidneys become detectable when excitation wavelength was longer than 600 nm. The highest ratio between kidney intensity and surrounding tissue intensity was obtained at Ex filter=710 nm. Therefore, Ex/Em filters of 710/830 nm were chosen in noninvasive kidney imaging with GS-AuNPs.

FIG. 20 shows whole-body fluorescence images of a mouse after intravenous injection with GS-AuNPs, sampled at different excitation wavelengths, and collected using an Em filter of 810 nm. The images demonstrate that the mouse's kidneys become detectable when the excitation wavelength exceeds 600 nm. The highest ratio between kidney fluorescence intensity and the fluorescence intensity of the surrounding tissue was obtained at Ex filter=710 nm. Therefore, Ex/Em filters of 710/830 nm were chosen in noninvasive kidney imaging with GS-AuNPs.

NIR-emitting GS-AuNPs were used for kidney functional imaging, and organic molecule IRDye 800CW carboxylate served as control (FIG. 15). Despite significant differences in their chemical structures, GS-AuNPs and IRDye 800CW carboxylate both possess similar NIR-excitable/NIR-emitting properties (FIGS. 16-19) and efficient renal clearance (Liu 2013). Therefore, the effect of light penetration depth and probe excretion route on the kidney functional imaging can be avoided in a comparison study.

FIG. 21 shows bright field and fluorescence images of mice injected intravenously with IRDye 800CW carboxylate and imaged using invasive and noninvasive methods (Ex/Em filters: 710/790 nm). The mice were prepared for invasive and noninvasive imaging using the procedures described above and were imaged accordingly before IRDye 800CW carboxylate was injected (Pre) and at 1 min, 5 min, and 60 min post injection. The bright field images were collected before dye was injected. Dashed white lines mark the area where the mouse's skin was removed in order to perform invasive imaging.

FIG. 22 shows time-course changes in mouse skin fluorescence intensity and in the percentage of contrast enhancement of left and right mouse kidneys following IRDye injection with 800CW carboxylate injection. The date in FIG. 22 was obtained via noninvasive imaging. N=3, mean±s.d.

FIG. 23 shows changes in the fluorescence intensity of the right kidneys (RK) and left kidneys (LK) of mice following IRDye 800CW carboxylate injection, obtained via invasive and noninvasive imaging.

IRDye 800CW carboxylate behaved similarly to Cy7 in that it only enabled noninvasive imaging of the mouse kidney for less than 5 min after injection (FIG. 21). Even during invasive imaging, IRDye 800CW fluorescence in the mouse's skin increased rapidly, quickly surpassing any detectable kidney fluorescence at the 5-minute mark and later.

FIG. 22 shows that at 0.6 min p.i., percentage contrast enhancement of the kidneys were at 67.6±7.1% for the left kidney (LK) and 49.9±9.0% for the right kidney (RK). However, the values dropped rapidly at approximately 12 min p.i., with the RK and LK plots both demonstrating single exponential decay kinetics (FIG. 22).

The decay half-lives of percentage contrast enhancement for IRDye 800CW in mouse kidneys, obtained through noninvasive imaging, are 4.2 min for LK and 4.5 min for RK (FIG. 22). These half-life values are faster than the clearance half-lives of IRDye 800CW from the same kidneys, which are 4.3 min (50.1%)/28.0 min (49.9%) for LK and 4.7 min (46.0%)/18.9 min (54.0%) for RK, as obtained from invasive imaging (FIG. 23). In other words, when performing noninvasive imaging of mouse kidneys using IRDye 800CW as contrast agent, the signal contrast that allows visualization of the kidneys degrades faster than the dye's rate of clearance from mouse kidneys. The degradation in image quality may be attributed to interference from fluorescent dye that has been taken up by the skin, resulting in background "skin fluorescence".

Skin fluorescence intensity, obtained via noninvasive imaging of a mouse injected with IRDye 800CW (FIG. 22), is halfway to saturation at 4.1 min (FIG. 22), which is comparable to the LK and RK half-lives (for percentage contrast enhancement) in the same plot. Due to strong interference from "skin fluorescence", despite high signal intensity from IRDye 800CW in mouse kidneys, noninvasive imaging with IRDye 800 failed to report dye uptake and excretion from the kidney and performed much worse than invasive imaging (FIG. 23). These results further confirmed that rapid accumulation and long retention of organic fluorophores in the skin, particularly in subcutaneous fat, is a general cause for their failure in the noninvasive kidney imaging.

FIG. 24 shows bright field and fluorescence images of a skin-removed mouse (for invasive fluorescence imaging) and an intact mouse (for noninvasive fluorescence imaging) before and after intravenous injection with NIR-emitting GS-AuNP contrast dye (Ex/Em filters: 710/830). The mice were prepared for invasive and noninvasive imaging using the procedures described above and were imaged accordingly. The bright field images were collected before GS-AuNPs were injected. Dashed white lines mark the area where the mouse's skin was removed in order to perform invasive imaging.

Figure 25:
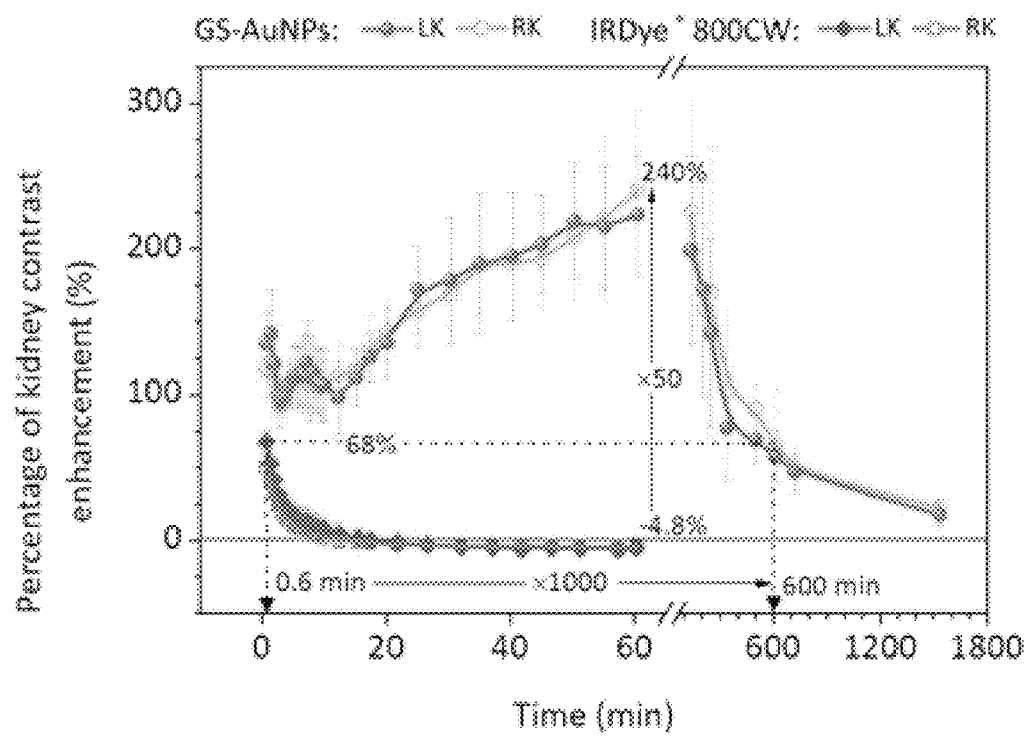
FIG. 25 compares changes in the percentage of contrast enhancement of mouse kidneys following injection with GS-AuNPs (left kidney shown in diamonds and right kidney shown in squares) and with IRDye 800CW (left kidney shown in filled circles and right kidney shown in open circles). N=3, mean±s.d.

FIG. 25 shows changes in the percentage of contrast enhancement of left kidneys (LK) and right kidneys (RK) in mice, obtained via noninvasive imaging following injection with either GS-AuNPs or IRDye 800CW. N=3, mean±s.d.

Figure 26:
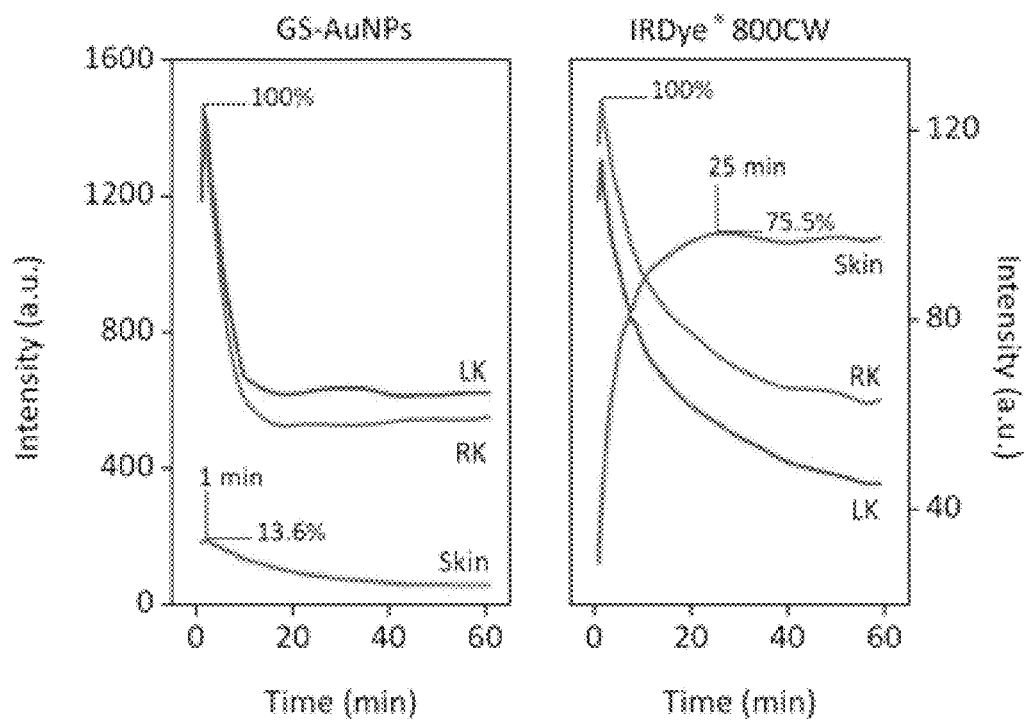
FIG. 26 shows the accumulation of GS-AuNPs and IRDye 800CW, both in mouse skins and in mouse kidneys, following intravenous injection. In order to detect the kidneys without interference from fluorescence originating from mouse skins, the fluorescence intensity values were obtained via invasive imaging.

FIG. 26 show the accumulation of GS-AuNPs and IRDye 800CW in mouse skins and mouse kidneys following intravenous injection, as measured using fluorescence intensity of the molecular probes. In order to detect the kidneys without interference from "skin fluorescence", the data used for these plots were obtained via invasive imaging.

In contrast to the transient nature of kidney visualization when using NIR organic dyes (e.g. Cy7 and IRDye 800CW), noninvasive kidney imaging using NIR-emitting GS-AuNPs has the advantage of a better kidney image (due to better contrast) and a longer detection window (FIG. 24). Invasive and noninvasive imaging using GS-AuNPs as contrast dye produced comparable images (FIG. 24). Within 12 min after injection of GS-AuNPs, percentage of contrast enhancement for mouse kidneys was in the range of 90% to 150% and gradually increased to maximum values of 240.0±55.3% (for LK) and 223.2±41.5% (for RK) at 60 min p.i., which is a much better than the corresponding values obtained from IRDye 800CW mice (−4.7±0.8% for LK and −4.8±5.1% for RK) (FIG. 25). The kidneys of mice injected with GS-AuNPs also remained detectable at 10 hours p.i., showing a percentage contrast enhancement of approximately 68% (FIG. 25). IRDye 800CW produces a similar enhancement at 0.6 min p.i. (FIG. 25), suggesting the detection time window for GS-AuNPs may be 1000 times longer than for IRDye 800CW.

The significant improvement in kidney image contrast and imaging detection time window achieved by GS-AuNPs may be attributed to (1) low skin accumulation of the hydrophilic GS-AuNPs, (2) their subsequent rapid clearance from the skin, and (3) high accumulation of the NPs in the kidney. In noninvasive imaging performed using GS-AuNP as contrast agent, skin fluorescence intensity peaked at 13.6±0.8% of maximum kidney fluorescence intensity (kidney fluorescence obtained from invasive imaging data, FIG. 26). Similar calculations for NIR-emitting organic dyes yield much higher ratios—95.3% for Cy7 and 75.5±9.3% for IRDye 800CW (FIG. 26). Additionally, GS-AuNPs accumulated in the skin faster and clear faster than the NIR-emitting organic dyes. Mice injected with GS-AuNPs reached maximum skin fluorescence intensity at ~1 min p.i., and then immediately decreased, following single exponential decay kinetics with a half-life of 12.6 min (FIG. 26). In comparison, mice injected with Cy7 reached the same skin fluorescence maximum at 35 min p.i. (FIG. 10) and IRDye 800CW at 25 min p.i. (FIG. 26). In other words, use of GS-AuNPs reduces the interference from background skin fluorescence typically seen when performing fluorescence imaging of kidneys using organic dyes.

Besides the GS-AuNP's low affinity for skin, its long retention in the blood also contributes to its prolonged detection time window as a contrast agent for noninvasive imaging. Since blood flow to the two kidneys is normally ~22% of cardiac output (Hall 2011; Liu 2013) and renal vascular supply is up to 47% of kidneys (Tobis 2012), the retention time and concentration of contrast agents in the blood play key roles in determining not only the kidney-contrast enhancements but also the imaging-time window. Pharmacokinetics studies have established that the elimination half-life ($t_{1/2\beta}$) of GS-AuNPs (8.5±2.1 h) in mice is 9 times longer than that of IRDye 800CW (0.98±0.08 h) (Liu 2013), thus allowing for extended noninvasive imaging of mouse kidneys until 10 hours p.i.

Validation of Fluorescence Renogram Obtained with GS-AuNPs

Figure 27:
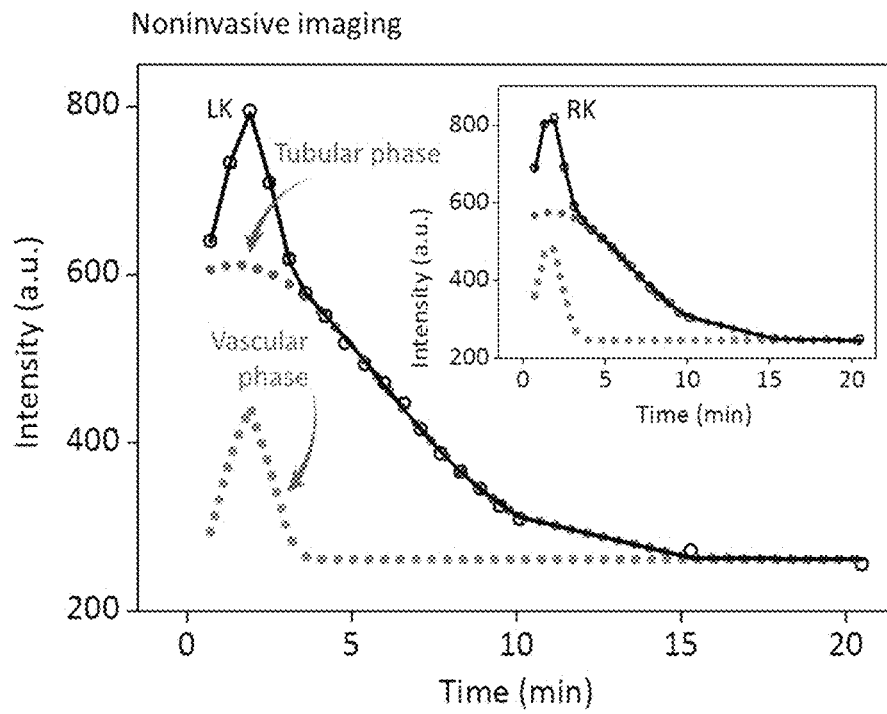
FIGS. 27 and 28 show time-fluorescence intensity curves obtained from noninvasive (FIG. 27) and invasive (FIG. 28) imaging of the right and left kidneys (RK and LK, respectively) of the same mouse (0-20 min p.i.) after intravenous injection of GS-AuNPs.
Figure 28:
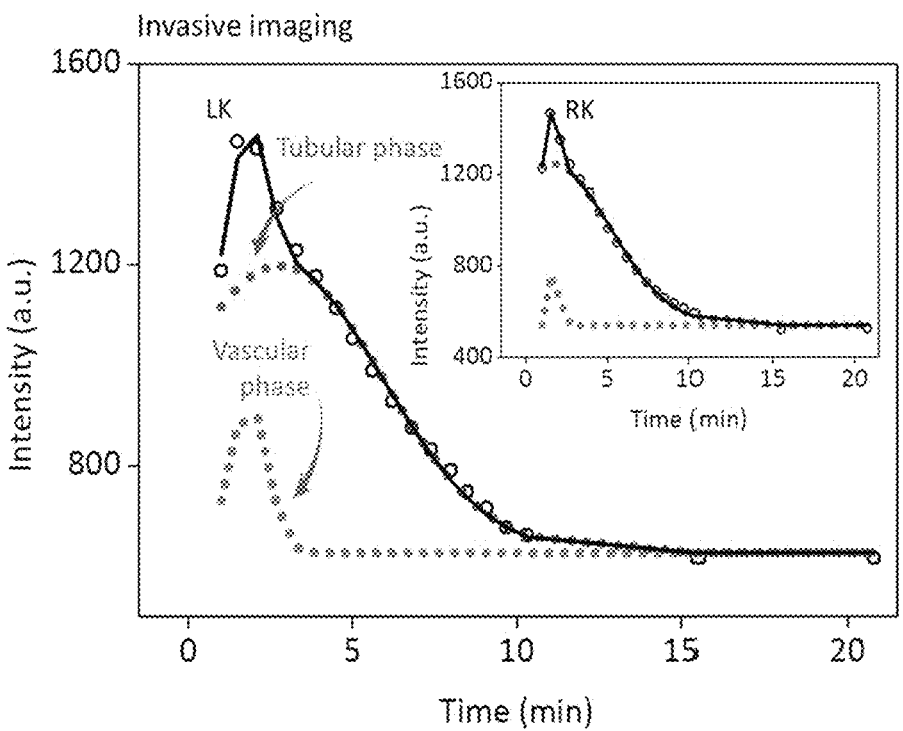

FIGS. 27 and 28 show time-fluorescence intensity curves (TFICs) obtained from noninvasive (FIG. 27) and invasive (FIG. 28) imaging of the right kidneys (RK) and left kidneys (LK) of mice injected with GS-AuNP. Also shown are the deconvolution of each of the fluorescence intensity curves into two peaks corresponding to the vascular phase and tubular phase of GS-AuNP clearance through the kidney.

FIGS. 29-35 show various parameters obtained from the deconvolution of the fluorescence intensity curves in FIGS. 27 and 28 into two peaks, corresponding to the vascular phase and the tubular phase of clearance through a mouse's kidney.

Figures 29, 30:
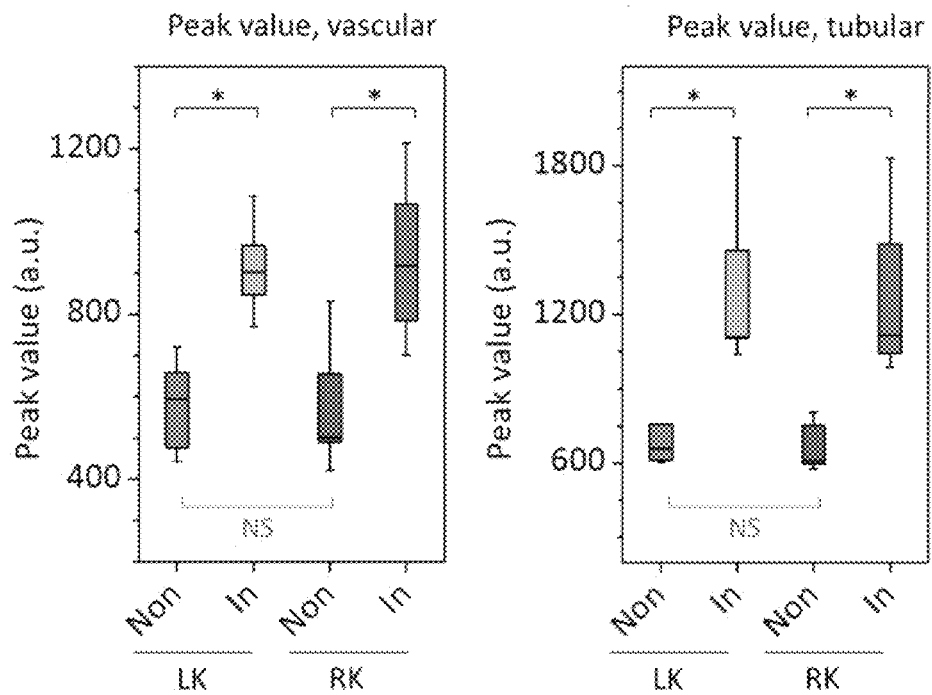
FIGS. 29-35 show results from the deconvolution of the fluorescence intensity curves in FIGS. 27 and 28 into two peaks, corresponding to the vascular phase and the tubular phase of clearance through a mouse's kidney. "LK" refers to the mouse's left kidney and "RK" to its right kidney.

FIG. 29 shows a statistical comparison of vascular phase peak values which were extracted from FIGS. 27 and 28. "*" indicates P<0.05.

FIG. 30 shows a statistical comparison of tubular phase peak values which were extracted from FIGS. 27 and 28. "*" indicates P<0.05.

Figure 31:
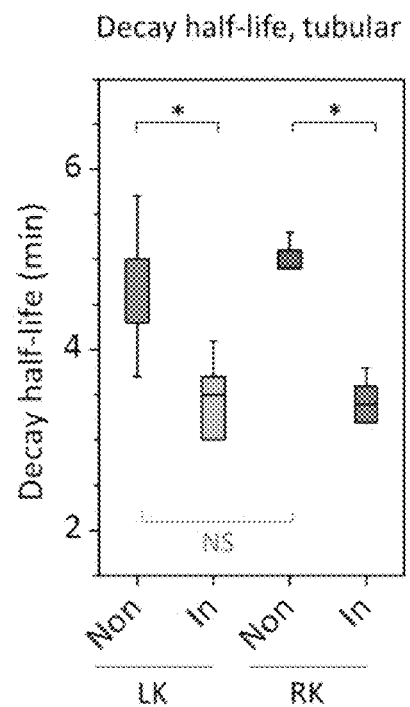

FIG. 31 shows a statistical comparison of the decay half-life values for the tubular phase of GS-AuNP clearance which were extracted from FIGS. 27 and 28. "*" indicates P<0.05.

Figure 32:
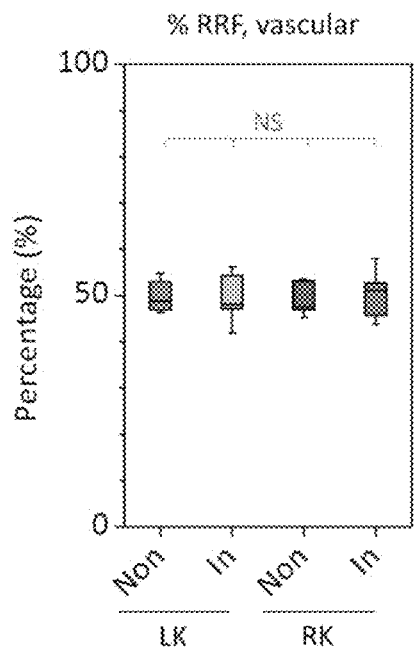

FIG. 32 shows a statistical comparison of the percentages of relative renal function (% RRF) in the vascular phase which were extracted from FIGS. 27 and 28. "NS" indicates that there is no significant difference between the values obtained from invasive and non-invasive imaging techniques.

Figure 33:
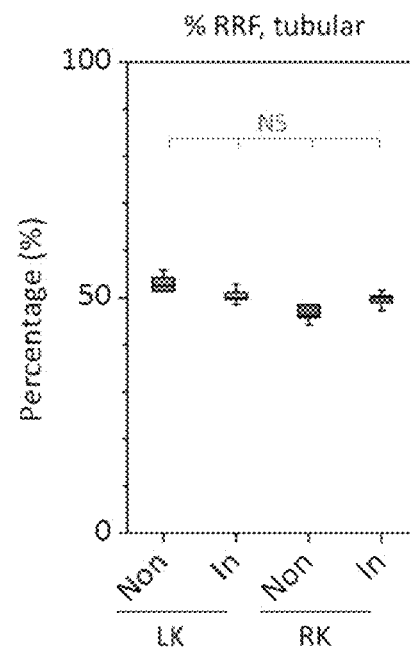

FIG. 33 shows a statistical comparison of the percentages of relative renal function (% RRF) in the tubular phase which were extracted from FIGS. 27 and 28. "NS" indicates that there is no significant difference between the values obtained from invasive and non-invasive imaging techniques.

Figure 34:
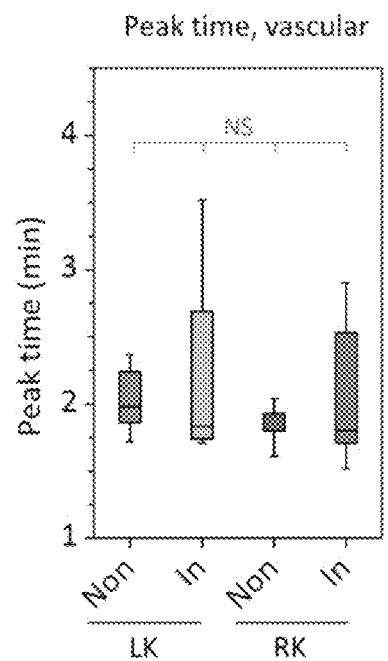

FIG. 34 shows a statistical comparison of the peak times in the vascular phase which were extracted from FIGS. 27 and 28. "NS" indicates that there is no significant difference between the values obtained from invasive and non-invasive imaging techniques.

Figure 35:
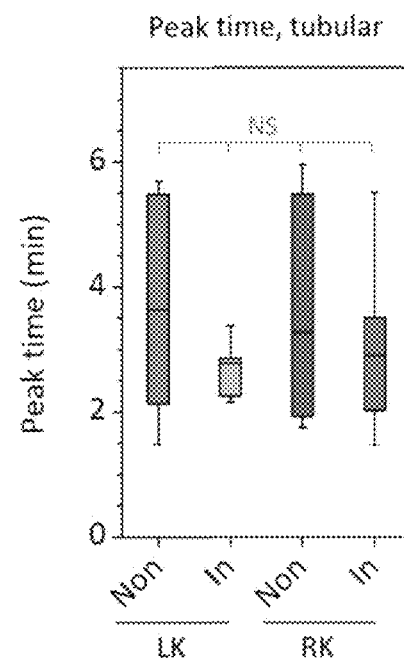

FIG. 35 shows a statistical comparison of the peak times in the tubular phase which were extracted from FIGS. 27 and 28. "NS" indicates that there is no significant difference between the values obtained from invasive and non-invasive imaging techniques.

To determine whether the kidney time-fluorescence intensity curves (TFICs) obtained noninvasively with GS-AuNPs can serve as renogram for evaluating kidney function, kidney TFICs were measured noninvasively (FIG. 27) and invasively (FIG. 28). Unlike organic dyes which show dramatic differences in kidney TFICs between noninvasive and invasive imaging (FIGS. 23, 13, and 14), the kidney TFICs obtained via noninvasive and invasive imaging methods show very similar profiles—a rapid ascending segment followed by a descending segment with two distinct decay kinetics (FIGS. 27 and 28). Further deconvolution of the TFICs in FIGS. 27 and 28 revealed two closely located peaks corresponding to the vascular and tubular phases identified in typical renograms (Conway 1992).

To quantitatively unravel the similarity and differences in kidney TFICs derived from noninvasive and invasive imaging (FIGS. 27 and 28), key parameters such as peak value, peak time, decay half-life and percentage of relative renal function (% RRF, percentage of overall intensity emitted from the left and right kidneys at peak value) were extracted from the two peaks. The peak values calculated from invasive imaging data were slightly higher than those with noninvasive imaging (p<0.05, FIGS. 29 and 30 and Table 1), likely because kidneys are well exposed to excitation light and to the camera when the mouse's skin has been removed. However, there was a difference of only ~1 min between the decay half-life of the tubular phase obtained via noninvasive and invasive imaging (p<0.05, FIG. 31). Furthermore, there was no significant difference between four of the parameters derived from the TFICs. That is, no significant difference between invasive and noninvasive imaging for tubular phase % RRF values (FIG. 33); vascular phase % RRF values (FIG. 32); vascular phase peak times (FIG. 34); and tubular phase peak times (FIG. 35).

In addition, LK and RK exhibited no differences in all the parameters (p>0.05, FIGS. 29-35), which is consistent with previous observations that the two kidneys in normal mice have equal function and were enhanced symmetrically in radiological imaging (Penna 2011; Tantawy 2012). These results suggest that in vivo fluorescence imaging with NIR-emitting GS-AuNPs as contrast agent can serve as alternative for noninvasive imaging of renogram.

Noninvasive Assessment of Kidney Function Changes in Mice with Unilateral Renal Disease Since changes in the GS-AuNP time-fluorescence intensity curves are directly associated with kidney dysfunction, application of noninvasive fluorescence renography in kidney disease diagnosis was subsequently investigated. The unilateral ureter obstruction (UUO) mouse model was utilized in the investigation. UUO is a preclinical model of ureteropelvic junction obstruction (UPJO) that is asymptomatic at an early stage but can cause renal failure if not treated promptly (Penna 2011). Renography is considered as the best means for diagnosing UPJO (Khan 2014; Conway 1992). UUO mice were generated by ligation of the left ureter while the right ureter was kept intact. Sham-operated mice were used as control. At 7-9 days post-operation, the UUO mice and sham control showed no significant difference in the levels of BUN and Scr, two of the most common biomarkers of renal function (p>0.05, Table 2). This result was consistent with previous findings that BUN and Scr were not good indicators of renal function in UUO model, owing to the presence of a contralateral kidney that functions well (Chung 2014; Ning 2013).

Figure 37:
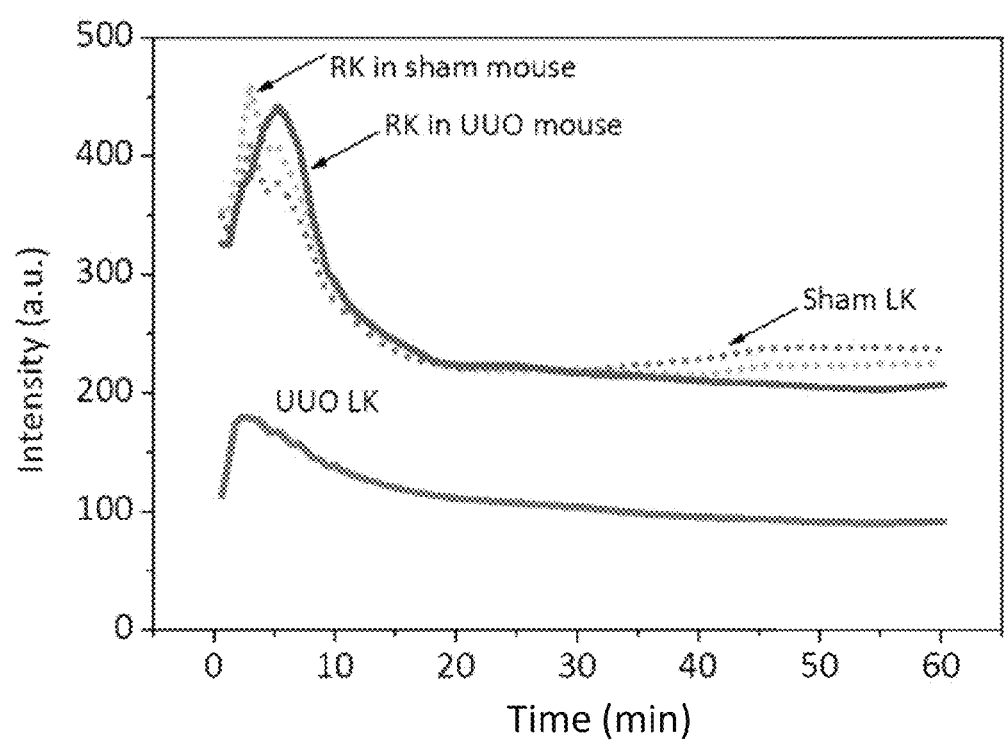

With assistance of noninvasive fluorescence images and TFIC/renogram curves, the UUO mice were easily distinguished from the sham control, and the UUO LK was easily differentiated from the normal contralateral kidney (FIGS. 36 and 37, and Table 3).

FIGS. 36-44 compare noninvasive fluorescence imaging of a unilateral ureter obstruction (UUO) mouse and a sham control mouse after intravenous injection of GS-AuNPs. The UUO mice were generated by ligation of the left ureter while the right ureter was kept intact.

FIG. 36 shows noninvasive fluorescence imaging of a unilateral ureter obstruction (UUO) mouse and a sham control mouse after intravenous injection of GS-AuNPs. The leftmost panels show bright field images of the mice prior to intravenous injection. The rest of the panels show noninvasive fluorescence images of the mice before injection with GS-AuNPs (Pre) and at 1 min, 5 min, and 60 min post injection. "LK" refers to the left kidney and "RK" refers to the right kidney.

FIG. 37 shows time-fluorescence intensity curves (TFICs) corresponding to the kidneys shown in FIG. 36. FIG. 37 shows the obstructed left kidney of a UUO mouse (UUO LK), the left kidney of a sham control mouse (Sham LK), and contralateral (unobstructed) right kidneys of the UUO mouse (RK in UUO mouse) and the sham mouse (RK in sham mouse) after intravenous injection of GS-AuNPs.

The obstructed LK (UUO LK in FIGS. 36 and 37) exhibited dramatically reduced fluorescence compared to the unobstructed contralateral RK in the same mouse (RK in UUO mouse) or the kidneys in the sham mouse (RK in UUO mouse and RK in sham mouse) (FIGS. 36 and 37). This outcome is consistent with renal function asymmetry of UUO model observed with nuclear imaging (Penna 2011, Tantawy 2011).

FIGS. 38-44 show an assessment of the functional change of each kidney of the UUO mouse by statistically comparing parameters extracted from the TFICs/renograms in FIG. 37. For FIGS. 38-44, N=6 for UUO mice, N=3 for sham control, mean±s.d., *P<0.05, P<0.01, *P<0.0001; NS, no significant difference.

Figure 38:
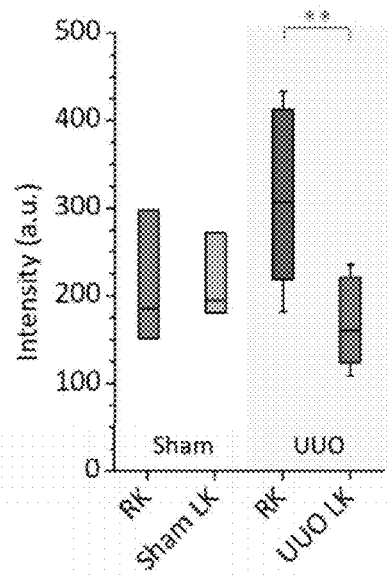
Figure 39:
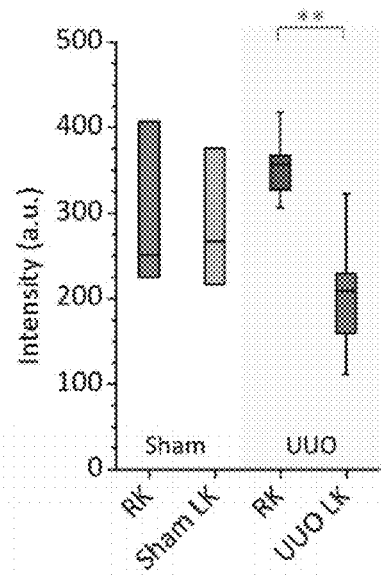

FIGS. 38 and 39 show peak values corresponding to the vascular (FIG. 38) and tubular (FIG. 39) phases of GS-AuNP clearance through the kidneys, extracted from the TFICs/renograms in FIG. 37.

Figure 40:
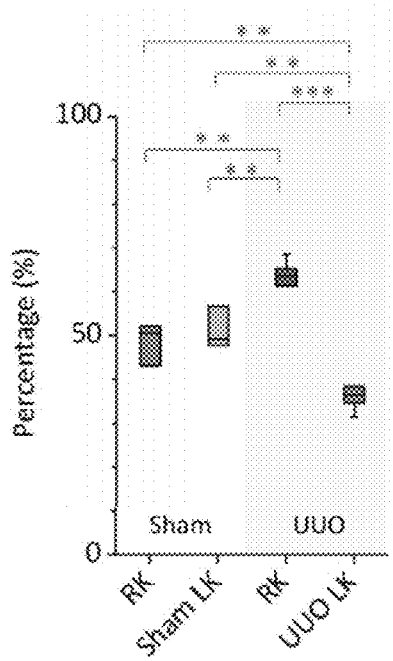
Figure 41:
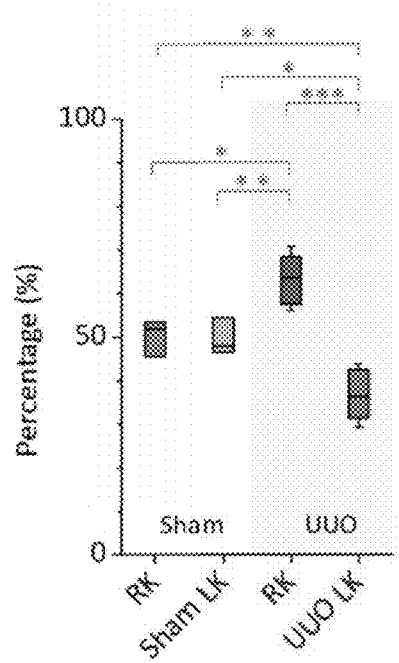

FIGS. 40 and 41 show percentage of relative renal function (% RRF) corresponding to the vascular (FIG. 40) and tubular (FIG. 41) phases of GS-AuNP clearance through the kidneys, extracted from the TFICs/renograms in FIG. 37.

Figure 42:
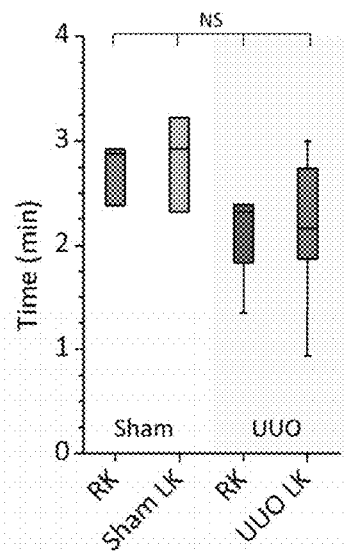
Figure 43:
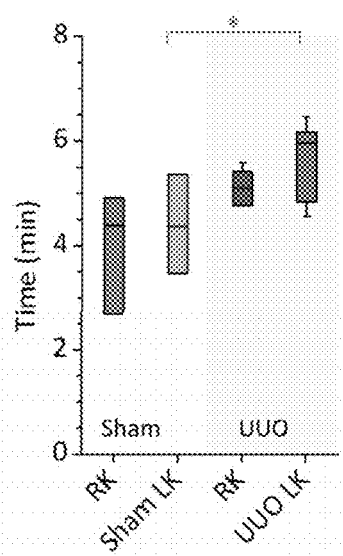

FIGS. 42 and 43 show peak times corresponding to the vascular (FIG. 42) and tubular (FIG. 43) phases of GS-AuNP clearance through the kidneys, extracted from the TFICs/renograms in FIG. 37.

Figure 44:
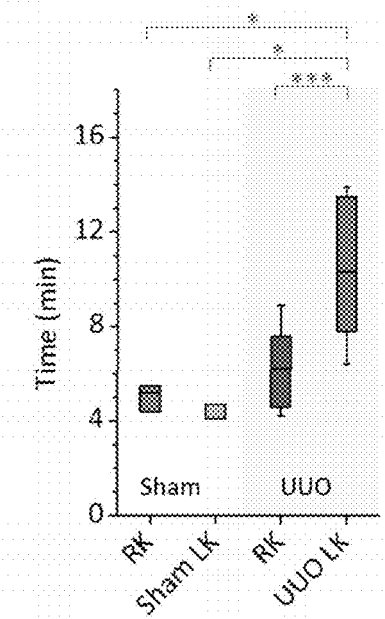

FIG. 44 shows decay half-lives corresponding to the tubular phase of GS-AuNP clearance through the kidneys, extracted from the TFICs/renograms in FIG. 37.

Figure 45:
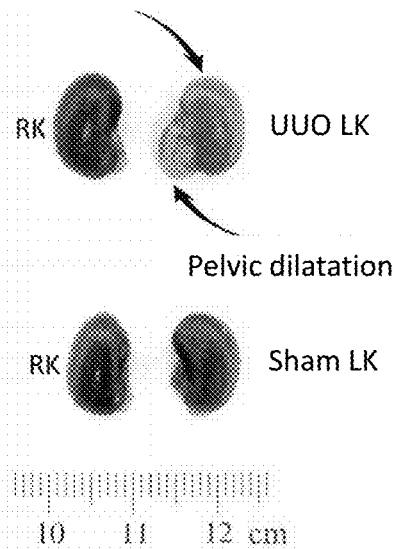

FIG. 45 shows ex vivo images of the sham mouse and UUO mouse kidneys characterized in FIGS. 36-44. The obstructed UUO LK showed characteristic reduced blood perfusion and pelvic dilatation while the contralateral RKs (UUO and sham) and sham LK remained normal.

Besides the remarkable decrease in the peak values of the obstructed LK compared with those of contralateral RK ($p<0.01$, FIGS. 38 and 39), parametric analysis of fluorescence renograms also showed that % RRF of UUO LK decreased to ~37%, below the level of unobstructed kidneys such as sham LK (~50%, $p<0.05$) and contralateral RK (~63%, $p<0.0001$) (FIGS. 40 and 41). Moreover, the peak time of tubular phase was also delayed in the obstructed LK (5.7±0.8 min) compared to that in sham LK (4.4±0.9 min, $p<0.05$, FIG. 43). In addition, the decay half-life of tubular phase was prolonged in UUO LK ($t_{1/2}$=10.4±3.0 min) compared with those of contralateral RK ($t_{1/2}$=6.3±2.0 min, $p<0.05$) and sham LK ($t_{1/2}$=4.5±0.3 min, $p<0.01$) (FIG. 44). Such a diminished and delayed accumulation of contrast agent in UUO kidney indicated the blood perfusion was dramatically reduced when obstruction occurred, consistent with previous findings in assessment of kidney function in UUO mouse using nuclear renogram. Ex vivo study further confirmed the characteristic reduced blood perfusion (pale-colored kidney) and pelvic dilatation of obstructed LK, whereas the contralateral RK and sham LK remained normal (FIG. 45).

Figure 46:
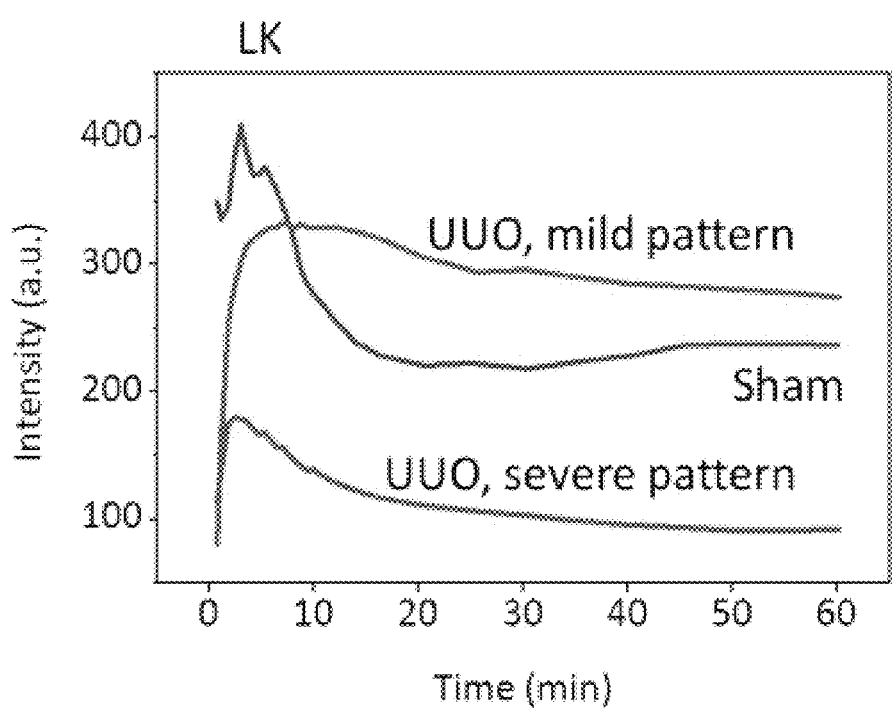
FIG. 46 shows time-fluorescence intensity curves (TFICs) of various mouse left kidneys (LK), obtained via noninvasive fluorescence imaging after GS-AuNP injection. UUO (mild pattern) is a UUO LK with mild to moderate damage, UUO (severe pattern) is a UUO RK with severe damage, and sham corresponds to a left kidney with no damage which originated from a sham mouse.

FIG. 46 shows time-fluorescence intensity curves (TFICs) of various mouse left kidneys (LK), obtained via noninvasive fluorescence imaging after GS-AuNP injection. UUO (mild pattern) is a UUO LK with mild to moderate damage, UUO (severe pattern) is a UUO RK with severe damage, and sham corresponds to a left kidney with no damage which originated from a sham mouse.

FIGS. 47 to 49 show pathologic analysis of UUO LKs and sham LK (H&E stain, scale bar=100 μm). The analysis revealed no damage to sham LK (FIG. 47), mild to moderate damage to UUO LK (mild pattern) (FIG. 48), and severe damage to UUO LK (severe pattern) (FIG. 49). In FIGS. 47 and 48, tubular atrophy is depicted by arrows and tubular dilatation by stars.

Figure 50:
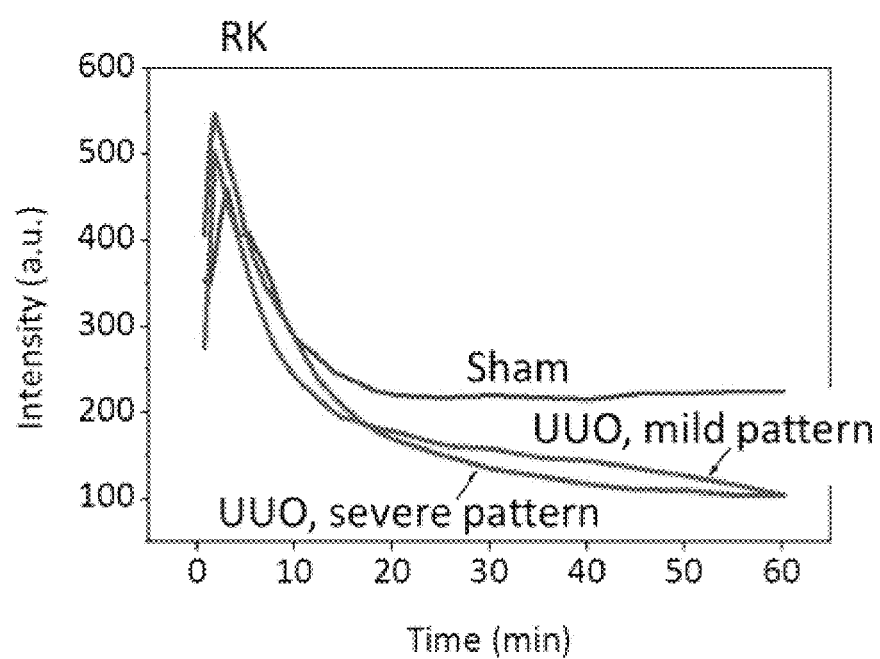
FIG. 50 shows TFICs/renograms of right kidneys (RKs) in UUO mice and in the sham mouse, obtained via noninvasive fluorescence imaging after GS-AuNP injection.

FIG. 50 shows TFICs/renograms of undamaged right kidneys (RKs) in UUO mice and in the sham mouse, obtained via noninvasive fluorescence imaging after GS-AuNP injection. Here, UUO (mild pattern) and UUO (severe pattern) do not describe the level of damage in the RK. Rather, they describe the level of damage observed in the each UUO mouse's corresponding obstructed left kidney. Sham corresponds to a right kidney with no damage originating from a sham mouse.

FIGS. 51 to 53 show pathologic analysis of RK in sham mouse (FIG. 51), RK in UUO mouse (mild pattern) (FIG. 52), and RK in UUO mouse (severe pattern) (FIG. 53) (H&E stain, scale bar=100 μm). Unlike the corresponding obstructed left kidneys, none of these right kidneys show any damage.

FIG. 54 shows fluorescence images of a mouse injected with NIR-emitting GS-AuNPs (Ex/Em filters: 710/830 nm) taken using noninvasive techniques at various time mouse in the 24-hour time span after intravenous injection. The first panel (Bright field) show a brightfield image of the mouse prior to intravenous injection. The rest of the panels show noninvasive fluorescence images of the mouse after 1 h, 2 h, 3.5 h, 4 h, 6 h, 8.5 h, 10 h, 12 h, and 24 h after injection with GS-AuNPs. A star marks the stomach of the mouse and arrows the mouse's intestines. Triangles point to the left kidney (LK) and right kidney (RK) of this mouse.

The percentage of kidney contrast enhancement during 1-24 h p.i. for these images is shown in FIG. 25. The kidneys remained detectable at 10 h p.i with a contrast enhancement of ~68%. IRDye 800 showed a comparable contrast enhancement value at 0.6 min p.i., but that value decreased rapidly thereafter.

FIGS. 55-57 show evaluation of fluorescence imaging of mouse kidneys (in a UUO mouse and in a sham mouse) after IRDye 800CW injection.

FIG. 55 shows brightfield images and fluorescence images of a UUO mouse (UUO) and a sham control (Sham) before and after intravenous injection of IRDye 800CW. The brightfield images (Bright field) were collected before GS-AuNPs were injected. These fluorescence images were taken before IRDye 800 CW was inject (Pre) and at 1 min, 5 min, 10 min, and 60 minutes post injection. Here, the UUO left kidney (LK) showed lower fluorescence intensity compared to contralateral right kidney (RK) at 1 min p.i. However, both UUO LK and RK disappeared after 5 min p.i. due to overwhelming fluorescence background from mouse skins skin (star). Dye molecules tended to accumulate in the skin scar area (arrow), where skin became thicker during recovery after surgery.

FIGS. 56-57 show the time-fluorescence intensity curves of LK, RK and skin of the sham control (FIG. 56) and the UUO mouse (FIG. 57), which were very similar in the profile.

In addition to identifying the obstructed kidney, the current method may be used to noninvasively differentiate degrees of hydronephrosis based on patterns of fluorescence renograms in fluorescence imaging. For example, as shown in FIGS. 38, 46, and 49, low peak values (such as for the damaged UUO LK, severe pattern) indicate a severe reduction in renal function. A lesser decrease in peak value corresponded to a relatively mild reduction in the renal function (mild pattern, FIG. 46).

As shown in the mild pattern, the peak value of UUO LK was only slightly reduced compared with sham LK, and a high percentage of peak value was maintained in the UUO LK for 60 min p.i. In H&E stained tissues, nucleus and cytoplasm were stained in violet and pink, respectively. Different form the pink color of normal kidneys (Sham LK, FIG. 47; contralateral RKs of Sham and UUO mice, FIG. 51-53), violet color was dominant in the UUO kidneys (FIGS. 48 and 49) and this color change directly reflected a loss of cytoplasm (cellular atrophy). For UUO LKs with two different renogram patterns, different degrees of renal damage were observed. In the mild pattern, the renal tubules showed mild to moderate atrophy and dilatation (FIGS. 47 and 48). Although the accumulation and excretion of NPs in kidney were slowed down, the observed high peak value of kidney fluorescence indicates that the blood perfusion was not significantly changed. On the other hand, in the severe pattern, the renal tubular damage and cortical atrophy were much more pronounced and the blood perfusion dramatically reduced, resulting in significant decrease in peak intensity of kidney fluorescence (FIG. 49). Interestingly, in the case of contralateral RKs of UUO mice, their fluorescence renograms also slightly changed compared with renogram of RKs in sham-operated mice (FIG. 50) even though no obvious structural changes were observed (FIG. 51-53). For sham mouse, the decrease of kidney intensity ended at 20 min p.i.; whereas a second clearance phase of contralateral RKs appeared during 15~60 min in UUO mice, following the initial decrease within ~15 min. Additionally, the % RRF of contralateral RK increased from the normal value of ~50% to 64% ($p<0.05$, FIG. 40,41). These changes in renograms of contralateral RKs implied an adaptive function of the unobstructed kidney when the other kidney is damaged. As control, IRDye 800 CW showed very similar profiles of time-dependent intensity curve in sham and UUO mice. (FIGS. 56-57).

Noninvasive Imaging Using GS-AuNPs, GS-AgNPs, and GS-Au/Ag-NPs

The antifouling nature of glutathione allowed quantitative investigation of renal clearance of these ultrasmall metal NPs without interference from protein adsorption. Four groups of BALB/c mice (N=3) were intravenously injected with the four types of metal NPs respectively, and urine samples were collected at various time points and then quantitatively analysed with ICP-MS.

Noninvasive monitoring of the fluorescence signal from kidneys and background tissues of BALB/c mice (N=3) after being injected with GS-AuNPs and GS-AgNPs, respectively. FIG. 58 shows the study of renal clearance kinetics and kidney penetration.

Figure 58A:
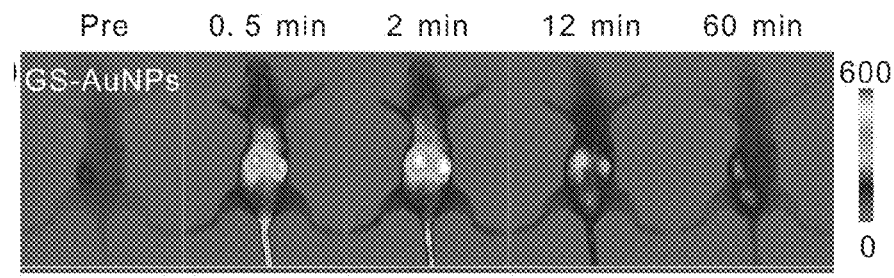
FIG. 58A shows noninvasive fluorescence images of the mice before injection with GS-AuNPs (Pre) and at 0.5 min, 2 min, 12 min and 60 min post injection (Ex/Em filters: 710/830 nm).

FIG. 58A shows a representative whole-body noninvasive fluorescence images of a mouse before injection with GS-AuNPs (Pre) and at 0.5 min, 2 min, 12, min and 60 post injection. (Ex/Em filters: 710/830 nm).

Figure 58B:
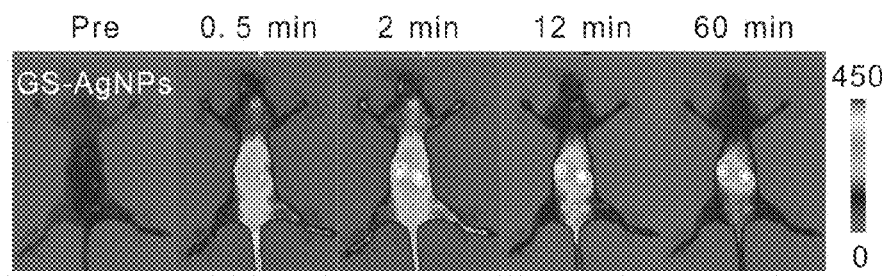
FIG. 58B shows noninvasive fluorescence images of the mice before injection with GS-AgNPs (Pre) and at 0.5 min, 2 min, 12 min and 60 min post injection (Ex/Em filters: 710/830 nm).

FIG. 58B shows a representative whole-body noninvasive fluorescence images of a mouse before injection with GS-AgNPs (Pre) and at 0.5 min, 2 min, 12, min and 60 post injection. (Ex/Em filters: 710/830 nm).

Figure 59A:
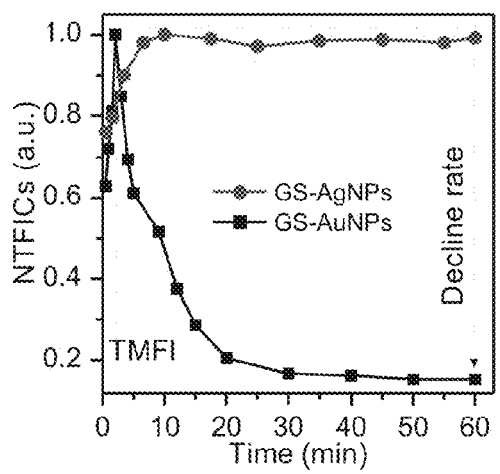
FIG. 59A shows representative time-fluorescence intensity curves (TFICs) of kidneys, obtained via noninvasive fluorescence imaging after intravenous injection of GS-AuNPs or GS-AgNPs (N=3).
Figure 59B:
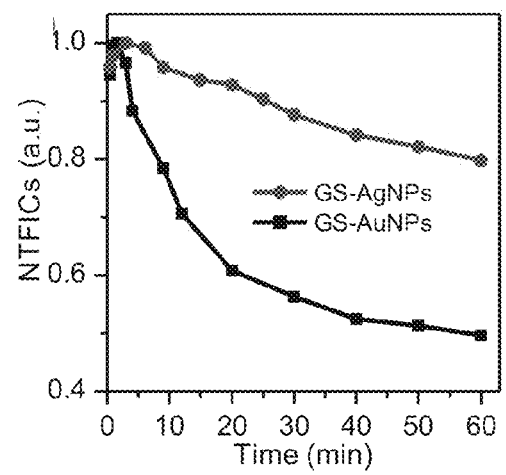
FIG. 59B shows representative time-fluorescence intensity curves (TFICs) of background, obtained via noninvasive fluorescence imaging after intravenous injection of GS-AuNPs or GS-AgNPs (N=3).

FIGS. 59A and 59B show representative time-fluorescence intensity curves (TFICs) of mouse kidneys (FIG. 59A) and mouse skin (or background) (FIG. 59B) in the two groups of BALB/c mice (N=3) intravenously injected with GS-AuNPs and GS-AgNPs. Two parameters were extracted from the kidney TFICs: time at maximum fluorescence intensity (TMFI) and decline rate (defined as the decline percentage at 60 min=[(peak value-intensity at 60 min)/peak value]×100%).

For mice injected with GS-AuNPs, the average fluorescence intensity of left and right kidney regions rapidly increased to the maximum value at about 2 min p.i. (FIG. 58A, 59A), followed by a rapid decrease. At 1 hr p.i., the kidney fluorescence signal was reduced to less than 20% of the maximum signal (FIG. 59A). On the other hand, for mice injected with GS-AgNPs, maximum fluorescence commenced at 11.83±1.75 min. Furthermore, the GS-AgNP fluorescence in the mouse kidneys remained at relatively constant intensity with only negligible decrease (1.43%), even though GS-AgNPs were eliminated more quickly into the bladder than GS-AuNPs during the same period.

The descriptions of the various embodiments of the present invention have been presented for purposes of illustration, but are not intended to be exhaustive or limited to the embodiments disclosed. Modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

REFERENCES

Alivisatos, A. P. Semiconductor clusters, nanocrystals, and quantum dots. Science 271, 933-937 (1996).

Choi, H. S., Gibbs, S. L., Lee, J. H., Kim, S. H., Ashitate, Y., Liu, F., Hyun, H., Park, G., Xie, Y., Bae, S., Henary, M. & Frangioni, J. V. Targeted zwitterionic near-infrared fluorophores for improved optical imaging. Nature Biotechnology 31, 148-153 (2013).

Choi, H. S., Liu, W., Misra, P., Tanaka, E., Zimmer, J. P., Ipe, B. I., Bawendi, M. G. & Frangioni, J. V. Renal clearance of quantum dots. Nature Biotechnology 25, 1165-1170 (2007).

Chou, L. Y. T., Zagorovsky, K. & Chan, W. C. W. DNA assembly of nanoparticle superstructures for controlled biological delivery and elimination. Nature Nanotechnology 9, 148-155 (2014).

Chung, S., Yoon, H., Kim, S., Kim, S., Koh, E., Hong, Y., Park, C., Chang, Y. & Shin, S. Oleanolic acid attenuates renal fibrosis in mice with unilateral ureteral obstruction via facilitating nuclear translocation of Nrf2. Nutrition & Metabolism 11, 2 (2014).

Conway, J. & Maizels, M. The Well Tempered Diuretic Renogram—A Standard Method to Examine the Asymptomatic Symptomatic Neonate with Hydronephrosis or Hydroureteronephrosis. J. Nucl. Med. 33, 2047-2051 (1992).

Du, Y., An, S., Liu, L., Li, L., Zhou, X. J., Mason, R. P. & Mohan, C. Serial Non-Invasive Monitoring of Renal Disease Following Immune-Mediated Injury Using Near-Infrared Optical Imaging. Plos One 7, e43941 (2012).

Frangioni, J. V. In vivo near-infrared fluorescence imaging. Current Opinion in Chemical Biology 7, 626-634 (2003).

Gao, X. H., Cui, Y. Y., Levenson, R. M., Chung, L. W. K. & Nie, S. M. In vivo cancer targeting and imaging with semiconductor quantum dots. Nature Biotechnology 22, 969-976 (2004).

Hall, J. E. Guyton and Hall Textbook of Medical Physiology, Edn. 12. (Saunders, 2011).

Hao, G., Du, Y., Zhou, X. J., Guo, J., Sun, X., Mohan, C. & Oez, O. K. Serial Non-Invasive Assessment of Antibody Induced Nephritis in Mice Using Positron Emission Tomography. Plos One 8 (2013).

Hilderbrand, S. A. & Weissleder, R. Near-infrared fluorescence: application to in vivo molecular imaging. Current Opinion in Chemical Biology 14, 71-79 (2010).

Hong, G., Diao, S., Chang, J., Antaris, A. L., Chen, C., Zhang, B., Zhao, S., Atochin, D. N., Huang, P. L., Andreasson, K. I., Kuo, C. J. & Dai, H. Through-skull fluorescence imaging of the brain in a new near-infrared window. Nature Photonics 8, 723-730 (2014).

James, M. T., Hemmelgarn, H. R. & Tonelli, M. Renal Medicine 2 Early recognition and prevention of chronic kidney disease. Lancet 375, 1296-1309 (2010).

Khan, F., Ahmed, K., Lee, N., Challacombe, B., Khan, M. S. & Dasgupta, P. Management of ureteropelvic junction obstruction in adults. Nat Rev Urol 11, 629-638 (2014).

Kiyose, K., Hanaoka, K., Oushiki, D., Nakamura, T., Kajimura, M., Suematsu, M., Nishimatsu, H., Yamane, T., Terai, T., Hirata, Y. & Nagano, T. Hypoxia-Sensitive Fluorescent Probes for in Vivo Real-Time Fluorescence Imaging of Acute Ischemia. Journal of the American Chemical Society 132, 15846-15848 (2010).

Liu, D., Poon, C., Lu, K., He, C. & Lin, W. Self-assembled nanoscale coordination polymers with trigger release properties for effective anticancer therapy. Nature Communications 5 (2014).

Liu, J., Yu, M., Zhou, C., Yang, S., Ning, X. & Zheng, J. Passive Tumor Targeting of Renal-Clearable Luminescent Gold Nanoparticles: Long Tumor Retention and Fast Normal Tissue Clearance. Journal of the American Chemical Society 135, 4978-81 (2013).

Lovell, J. F., Jin, C. S., Huynh, E., Jin, H., Kim, C., Rubinstein, J. L., Chan, W. C. W., Cao, W., Wang, L. V. & Zheng, G. Porphysome nanovesicles generated by porphyrin bilayers for use as multimodal biophotonic contrast agents. Nature Materials 10, 324-332 (2011).

Nakamura, K. & Tabata, Y. A new fluorescent imaging of renal inflammation with RCP. Journal of Controlled Release 148, 351-358 (2010).

Ning, X.-h., Ge, X.-f., Cui, Y. & An, H.-x. Ulinastatin inhibits unilateral ureteral obstruction-induced renal interstitial fibrosis in rats via transforming growth factor β (TGF-β)/Smad signalling pathways. International Immunopharmacology 15, 406-413 (2013).

Park, J. H., Gu, L., von Maltzahn, G., Ruoslahti, E., Bhatia, S. N. & Sailor, M. J. Biodegradable luminescent porous silicon nanoparticles for in vivo applications. Nature Materials 8, 331-336 (2009).

Penna, F. J., Chow, J. S., Minnillo, B. J., Passerotti, C. C., Barnewolt, C. E., Treves, S. T., Fahey, F. H., Dunning, P. S., Freilich, D. A., Retik, A. B. & Nguyen, H. T. Identifying Ureteropelvic Junction Obstruction by Fluorescence Imaging: A Comparative Study of Imaging Modalities to Assess Renal Function and Degree of Obstruction in a Mouse Model. Journal of Urology 185, 2405-2413 (2011).

Radiological imaging of the kidney, Edn. 1. (Springer Berlin Heidelberg, 2011).

Roberts, J., Chen, B., Curtis, L. M., Agarwal, A., Sanders, P. W. & Zinn, K. R. Detection of early changes in renal function using (99m)Tc-MAG3 imaging in a murine model of ischemia-reperfusion injury. American Journal of Physiology-Renal Physiology 293, F1408-F1412 (2007).

Rowe, C. K., Franco, F. B., Barbosa, J. A. B. A., Minnillo, B. J., Chow, J. S., Treves, T., Retik, A. B. & Nguyen, H. T. A Novel Method of Evaluating Ureteropelvic Junction Obstruction: Dynamic Near Infrared Fluorescence Imaging Compared to Standard Modalities to Assess Urinary Obstruction in a Swine Model. Journal of Urology 188, 1978-1985 (2012).

Shuhendler, A. J., Pu, K., Cui, L., Uetrecht, J. P. & Rao, J. Real-time imaging of oxidative and nitrosative stress in the liver of live animals for drug-toxicity testing. Nature Biotechnology 32, 373-U240 (2014).

Sun, Y. P., Zhou, B., Lin, Y., Wang, W., Fernando, K. A. S., Pathak, P., Meziani, M. J., Harruff, B. A., Wang, X., Wang, H. F., Luo, P. J. G., Yang, H., Kose, M. E., Chen, B. L., Veca, L. M. & Xie, S. Y. Quantum-sized carbon dots for bright and colorful photoluminescence. Journal of the American Chemical Society 128, 7756-7757 (2006).

Szabo, Z., Alachkar, N., Xia, J. S., Mathews, W. B. & Rabb, H. Molecular Imaging of the Kidneys. Seminars in Nuclear Medicine 41, 20-28 (2011).

Tantawy, M. N., Jiang, R., Wang, F., Takahashi, K., Peterson, T. E., Zemel, D., Hao, C.-M., Fujita, H., Harris, R. C., Quarles, C. C. & Takahashi, T. Assessment of renal function in mice with unilateral ureteral obstruction using Tc-99m-MAG3 dynamic scintigraphy. Bmc Nephrology 13 (2012).

Tobis S, K. J., Silvers C R, Marshall J, Cardin A, Wood R W, Reeder J E, Erturk E, Madeb R, Yao J, Singer E A, Rashid H, Wu G, Messing E, Golijanin D. Near infrared fluorescence imaging after intravenous indocyanine green: initial clinical experience with open partial nephrectomy for renal cortical tumors. Urology 79, 7 (2012).

Vlasov, Shiryaev, A. A., Rendler, T., Steinert, S., Lee, S.-Y., Antonov, D., Voeroes, M., Jelezko, F., Fisenko, A. V., Semjonova, L. F., Biskupek, J., Kaiser, U., Lebedev, O. I., Sildos, I., Hemmer, P. R., Konov, V. I., Gali, A. & Wrachtrup, J. Molecular-sized fluorescent nanodiamonds. Nature Nanotechnology 9, 54-58 (2014).

Weissleder, R. & Pittet, M. J. Imaging in the era of molecular oncology. Nature 452, 580-589 (2008).

Wilson, W. L., Szajowski, P. F. & Brus, L. E. Quantum Confinement in Size-Selected, Surface-Oxidized Silicon Nanocrystals. Science 262, 1242-1244 (1993).

Yu, M., Zhou, C., Liu, J., Hankins, J. D. & Zheng, J. Luminescent Gold Nanoparticles with pH-Dependent Membrane Adsorption. Journal of the American Chemical Society 133, 11014-11017 (2011).

Zheng, J., Nicovich, P. R. & Dickson, R. M. Highly fluorescent noble-metal quantum dots. Annual Review of Physical Chemistry 58, 409-431 (2007).

Zheng, J., Zhou, C., Yu, M. & Liu, J. Different sized luminescent gold nanoparticles. Nanoscale 4, 4073-4083 (2012).

Zhou, C. Hao, G. Y. Thomas, P. Liu, J. B. Yu, M. X. Sun, S. S., Oz, O. K., Sun, X. K. & Zheng, J. Near-Infrared Emitting Radioactive Gold Nanoparticles with Molecular Pharmacokinetics. Angewandte Chemie-International Edition 51, 10118-10122 (2012).

Zhou, C., Long, M., Qin, Y., Sun, X. & Zheng, J. Luminescent Gold Nanoparticles with Efficient Renal Clearance. Angewandte Chemie-International Edition 50, 3168-3172 (2011).

Zhou, C., Sun, C., Yu, M., Qin, Y., Wang, J., Kim, M. & Zheng, J. Luminescent Gold Nanoparticles with Mixed Valence States Generated from Dissociation of Polymeric Au(I) Thiolates. The Journal of Physical Chemistry C 114, 7727-7732 (2010).

What is claimed is:

1. A non-invasive method for evaluating renal function of an individual kidney in a living subject, the method comprising:

a) intravenously administering nanoparticles of noble metal to a kidney of the live subject;

b) illuminating the kidney with a near infrared excitation wavelength such that the nanoparticles in the kidney fluoresce; and c) detecting presence or absence of nanoparticle fluorescence in the kidney of the live subject, wherein detecting presence or absence of nanoparticle fluorescence includes obtaining at least one image of the kidney through the subject's skin.

2. The method of claim 1, wherein taking at least one image of the kidney includes taking sequential images within an evaluation time window.

3. The method of claim 2, wherein the length of the evaluation time window is between 1 second and 10 hours.

4. The method of claim 2, further comprising:

d) plotting a time-fluorescence intensity curve (TFIC) for the kidney, wherein an axis of the time-fluorescence intensity curve is time and another axis of the time-fluorescence intensity curve is kidney fluorescence intensity.

5. The method of claim 1, wherein the nanoparticles fluoresce at a near infrared emission wavelength.

6. The method of claim 1, wherein the noble metal is selected from a group consisting of gold, silver, copper, or combinations thereof.

7. The method of claim 1, wherein the nanoparticles have a core size of less than 6 nm.

8. The method of claim 1, wherein the nanoparticles have a core size between 1 nm and 4 nm.

9. The method of claim 1, wherein the nanoparticles have a hydrodynamic diameter less than 10 nm.

10. The method of claim 1, wherein the nanoparticles have a hydrodynamic diameter between 1 nm and 6 nm.

11. The method of claim 1, wherein the nanoparticles are coated with ligands selected from glutathione, thiol-functionalized polyethylene glycol, cysteamine, cysteine, homocysteine, dipeptides containing cysteine, dipeptides containing homocysteine, dipeptides, tripeptides, and combinations thereof.

12. The method of claim 11, wherein dipeptides containing cysteine includes cysteine-glycine and cysteine-glutamic acid and dipeptides containing homocysteine includes homocysteine-glycine and homocysteine-glutamic acid.

13. The method of claim 1, wherein the nanoparticles are coated with glutathione.

14. A system for non-invasive evaluation of renal function of an individual kidney in a living subject comprising:

a) intravenous administration of nanoparticles of a noble metal to a kidney of the live subject;

b) illumination of the kidney with a near infrared excitation wavelength such that the nanoparticles in the kidney fluoresce; and c) detection of presence or absence of nanoparticle fluorescence in the kidney of the live subject, wherein detection includes obtaining at least one image of the kidney through the subject's skin.

15. The system of claim 14, wherein taking at least one image of the kidney includes taking sequential images within an evaluation time window.

16. The system of claim 15, wherein the length of the evaluation time window is between 1 second and 24 hours.

17. The system of claim 14, wherein the nanoparticles are nanoparticles of a noble metal and the noble metal is selected from a group consisting of gold, silver, copper, or combinations thereof, wherein the nanoparticles fluoresce at a near infrared emission wavelength, and wherein the nanoparticles are coated with ligands selected from glutathione, thiol-functionalized polyethylene glycol, cysteamine, cysteine, homocysteine, dipeptides containing cysteine, dipeptides containing homocysteine, dipeptides, tripeptides, and combinations thereof.

18. A kit comprising: an amount of renal clearable, nanoparticles of a noble metal in a sealed container, wherein the amount of the nanoparticles is suitable for imaging a kidney of a mammal, and instructions for the use thereof in imaging said kidney, the instructions comprising the steps of:

a) administering renal clearable nanoparticles of a noble metal to a kidney of the live subject, wherein the noble metal is selected from a group consisting of gold, silver, copper, platinum, palladium, or combinations thereof;

b) illuminating the kidney with a near infrared excitation wavelength such that the nanoparticles in the kidney fluoresce; and c) detecting presence or absence of nanoparticle fluorescence in the kidney of the live subject, wherein detecting presence or absence of nanoparticle fluorescence includes obtaining at least one image of the kidney through the subject's skin wherein taking at least one image of the kidney includes taking sequential images and the sequential images are collected at time intervals within an evaluation time window.

19. The method of claim 4, further comprising:

(i) deconvoluting the TFIC into a first component curve and a second component curve, the first component curve corresponding to a vascular phase of nanoparticle clearance from the kidney and the second component curve corresponding to tubular phase of nanoparticle clearance from the same kidney;

(ii) fitting the TFIC, first component curve, and/or second component curve to an exponential decay function, wherein the exponential decay function is either a single exponential decay function or a double exponential decay function; and (iii) extracting at least one curve parameter value from the exponential decay function, wherein the curve parameter value is selected from a group consisting of peak value, peak time, decay half-life, and a percentage of relative renal function value.

20. The method of claim 19, further comprising comparing the at least one curve parameter value with a corresponding control curve parameter value, wherein the control curve parameter value is obtained from a control animal, wherein a statistically significant increase in the at least one curve parameter value when compared to the control curve parameter value indicates presence of renal function changes.

* * * * *